(12) United States Patent
Ekramoddoullah et al.

(10) Patent No.: US 7,285,656 B2
(45) Date of Patent: Oct. 23, 2007

(54) ROOT-SPECIFIC CONIFER GENE PROMOTER AND ITS USE

(75) Inventors: Abul M. K. Ekramoddoullah, Victoria (CA); Jun-Jun Liu, Victoria (CA)

(73) Assignee: Her Majesty the Queen in Right of Canada, as represented by the Minister of Natural Resources Canada, Canadian Forest Service

( * ) Notice: Subject to any disclaimer, the term of this patent is extended or adjusted under 35 U.S.C. 154(b) by 339 days.

(21) Appl. No.: 10/422,714

(22) Filed: Apr. 25, 2003

(65) Prior Publication Data

US 2004/0019934 A1 Jan. 29, 2004

Related U.S. Application Data

(60) Provisional application No. 60/375,440, filed on Apr. 26, 2002.

(51) Int. Cl.
*C12N 15/82* (2006.01)

(52) U.S. Cl. .................. 536/24.1; 435/320.1

(58) Field of Classification Search ............... 536/24.1
See application file for complete search history.

(56) References Cited

OTHER PUBLICATIONS

Kim Y. et al. (A 20 nucleotide upstream element is essential for the nopaline synthase (nos) promoter activity. Plant Mol Biol. Jan. 1994;24(1):105-17).*
Yanagisawa S. Dof1 and Dof2 transcription factors are associated with expression of multiple genes involved in carbon metabolism in maize. Plant J. Feb. 2000;21(3):281-8.*
Yanagisawa S. et al. Involvement of maize Dof zinc finger proteins in tissue-specific and light-regulated gene expression. Plant Cell. Jan. 1998;10(1):75-89.*
Shen Q. et al. Modular nature of abscisic acid (ABA) response complexes: composite promoter units that are necessary and sufficient for ABA induction of gene expression in barley. Plant Cell. Jul. 1996;8(7):1107-19.*
Curie C. et al. Modular organization and development activity of an Arabidopsis thaliana EF-1 alpha gene promoter. Mol Gen Genet. Apr. 1993;238(3):428-36.*

* cited by examiner

*Primary Examiner*—Cynthia Collins
(74) *Attorney, Agent, or Firm*—Margaret McKay

(57) ABSTRACT

There is provided an isolated polynucleotide sequence useful as a promoter in plant root tissue. The sequence is derived from the promoter for the Western white pine gene PR10. The sequence comprises at least 45 nucleotides, and has at least two Dof elements which individually may be in a forward or inverted orientation. Each Dof element has a sequence NNNWAAAGNNN, wherein N is A, T, G, or, C, and, W is A or T. The Dof elements are separated from each other by between 10 and 20 nucleotides. The sequence also has a TATA box located between 15 and 25 nucleotides in the 3' direction of the closest Dof element. In some instances, the polynucleotide has one Dof element with the sequence NNNWAAAGNNN and another with the sequence NNNCTTTWNNN. In some instances the polynucleotide sequence is one where the 5' Dof element sequence is CTCTCTTTAAT, and another Dof element (which may be the next Dof element) sequence is TTTAAAGGTT and the TATA box sequence is TACAATAAATA or TATAWAWA, wherein W is A or T. Also provided are sequences useful in modulating gene expression in stem and leaf tissue.

6 Claims, 9 Drawing Sheets

ROOT-SPECIFIC CONIFER GENE PROMOTER AND ITS USE

This application claims priority of Apr. 26, 2002 from U.S. No. 60/375,440.

BACKGROUND OF THE INVENTION

A promoter is a DNA sequence located in the flanking regions of a gene. Expression of a gene is initiated at a gene transcription site, which in turn mainly depends on the RNA polymerase and cis-regulatory elements in the promoter regions.

Root tissue is very important in plant development. However, the state of the art with respect to understanding the regulation of gene expression in roots is still very limited. Cis-regulatory elements of promoters that exclusively confer root-specific expression have not been described in the literature, and only a few root-specific promoters have been described at all. Recently, an Arabidopsis gene (pyk10) promoter has been reported to drive gene expression in root in mature transgenic plants, but there is also extensive expression in different parts of a seedling (Nitz et al 2001 *Plant Sci.* 161: 337-346). Short elements that contribute to root-preferred expression have been revealed and been shown to be involved predominantly in root-specific expression as enhancers, such as the ocs-elements, ocs-like mas-elements and as-l-elements (Ellis et al 1987, EMBOJ., 6 :3203-3208; Feltkamp et al. 1995, Plant Sci. 109 :57-65; Lam et al., 1989, PNAS (USA), 86 :7890-7894.)

Tissue-specific expression is believed to be due to the interaction of a set of regulatory proteins that bind to a special combinatory set of cis-regulatory elements of the promoter. Therefore, the expression pattern of a designed gene is determined by trans-factors, the transcription factor proteins available from the background cells and cis-factors the cis-regulatory elements in the DNA sequences of gene regions. Most of cis-regulatory elements are located in the proximal region about 500 bp from the transcription start site. But some of them are found in the intron, coding region and downstream region, or in the distal region as far as 10 kb from start codon.

Root specific promoters are of special interest because of physiological functions in root and its vulnerability to many pathogens and pests.

Genetic engineering techniques provide a method to introduce useful traits to plants, but require a variety of tissue-specific promoters to express heterogeneous genes in the appropriate plant tissues. Root-specific promoters would have potential applications to promote expression of endogenous or heterogeneous genes in roots to enhance plant resistance to pathogens and pests; stress tolerance to heat, salt or drought; and improve absorbency of soil nutrients; and production of recombinant proteins aimed at molecular farming and phytoremediation.

Transgenic plants expressing polypeptides with anti-pathogen or anti-pest activity can be used to decrease crop or forest damage and loss. However, high levels of heterogeneous gene expression in other parts of plants may cause negative effects on plant growth and reproduction, and also cause selective pressure for pathogens or pests to develop resistance. Accordingly, tissue-specific expression is desirable in most cases of plant genetic engineering. Only a few promoters from angiosperms have been identified to be expressed in root tissues. (For example, see: U.S. Pat. No. 5,023,179, WO0153,502, U.S. Pat. No. 5,459,252, and U.S. Pat. No. 5,837,876.) These are angiosperm promoters whose function in gymnosperms is unknown Thus, it is an object of the invention to provide a promoter suitable for use in plant cells.

SUMMARY OF THE INVENTION

The isolation, genomic organization and molecular characterization of a novel member of PR10 gene family (PmPR10-1.14) in western white pine lead to the identification and characterization of the promoter of PmPR10-1.14 which is responsible for gene regulation in a root-specific manner. The sequence of this gene is shown in FIG. 1 and SEQ.ID.NO. 20. The sequence of the full length promoter is shown in SEQ.ID.NO.1.

As the first root-specific promoter cloned from a gymnosperm and from tree and functioned in angiosperm, the promoter of PmPR10-1.14 and variants thereof have potential usages in both angiosperms and gymnosperms, including agricultural species and forestry species.

In an embodiment of the invention there is provided an isolated polynucleotide sequence comprising SEQ.ID.NO. 2 or a variant at least 70%, 80% or 90% homologous thereto. In some instances, the polynucleotide is SEQ.ID.NO.7 or a variant at least 70%, 80% or 90% homologous thereto. In some instances the polynucleotide is SEQ.ID.NO.5 or a variant at least 70%, 80% or 90% homologous thereto.

In an embodiment of the invention there is provided an isolated polynucleotide sequence useful as a promoter in root tissue. The sequence comprises at least 45 nucleotides, and has at least two Dof elements which individually may be in a forward or inverted orientation. Each Dof element has a sequence NNNWAAAGNNN (SEQ ID No. 23), wherein N is A, T, G, or, C, and, W is A or T. The Dof elements are separated from each other by between 10 and 20 nucleotides. The sequence also has a TATA box located between 15 and 25 nucleotides in the 3' direction of the closest Dof element. In some instances, the polynucleotide has one Dof element with the sequence NNNWAAAGNNN and another with the sequence NNNCTTTWNNN. In some instances the polynucleotide sequence is one where the 5' Dof element sequence is CTCTCTTTAAT, and another Dof element (which may be the next Dof element) sequence is TTT-TAAAGGTT and the TATA box sequence is TACAATAAATA or TATAWAWA, wherein W is A or T. In some instances the polynucleotide is at least 80% homologous to a continuous region of SEQ.ID.NO.2 having substantially the same number of nucleolides.

In an embodiment of the invention there is provided a polynucleotide sequence useful in reducing expression of a downstream gene, said polynucleotide sequence comprising two copies of a DNA region each being independently at least 70%, 80% or 90% homologous to a region of substantially equal length containing at least 150 nucleotides (preferably at least 200 nucleotides, more preferably at least 250 nucleotides) contained between nucleotides −1326 and −1048 of SEQ.ID.NO. 20 as depicted in FIG. 1 (nucleotides 361 to 639 as numbered in SEQ.ID.NO 1), said copies being separated by between 0 and 100 nucleotides. In some instances the copies are separated by between 0 and 50 nucleotides. In some instances the copies are separated by between 0 and 20 nucleotides.

In an embodiment of the invention there is provided an isolated polynucleotide sequence useful in driving expression of a downstream gene. The polynucleotide contains a region of between 100 and 200 nucleotides in length which is at least 70%, 80% or 90% homologous to a portion of SEQ.ID.NO.21 or SEQ.ID.NO. 22 of substantially equal length.

In an embodiment of the invention there is provided a method of obtaining expression of a gene of interest in root tissue. The method comprises:

a) obtaining the gene of interest
b) generating a nucleotide construct having a promoter including SEQ.ID.NO.2 or a variant thereof located upstream of and proximal to the gene of interest;
c) introducing the construct into a plant cell in an expressible manner; and
d) generating root tissue from the plant cell.

The method may be used to express a gene which is an antifungal gene, a gene involved in nitrogen fixation, a gene related to drought or salt tolerance, a gene involved in potassium or sodium transport or metabolism, a gene involved in nutrient uptake or metabolism in root, or a gene encoding an antigen useful as a vaccine, including an edible vaccine for use in mammals. The method may be used to produce transgenic cells, plants and seeds containing the gene of interest in a manner suitable for eventual expression in root tissue.

In an embodiment of the invention there is provided a transgenic plant cell, plant, plant part, plant tissue, or seed comprising a polynucleotide sequence which is the sequence of SEQ.ID.NO. 2, 5, 7, or a variant thereof. In an embodiment of the invention there is provided a transgenic plant cell comprising a polynucleotide sequence which comprises at least 45 nucleotides, and has at least two Dof elements which individually may be in a forward or inverted orientation. Each Dof element has a sequence NNNWAAAGNNN, wherein N is A, T, G, or, C, and W is A or T (SEQ ID No. 23). The Dof elements are separated from each other by between 10 and 20 nucleotides. The sequence also has a TATA box located between 15 and 25 nucleotides in the 3' direction of the closest Dof element. The plant may be an angiosperm or a gymnosperm.

In an embodiment of the invention there is provided an isolated polynucleotide sequence comprising a region of at least 100 contiguous nucleotides. This region is at least 70%, 80% or 90% homologous to a 100 nucleotide region of SEQ.ID.NO.21 or SEQ.ID.NO.22. In some instance the region will be between 100 and 20 nucleotides long.

According to one aspect of the invention, a novel issue-specific promoter expressed predominately in the development of lateral roots is provided which has been isolated from the upstream non-coding region of western white pine PR10 gene. This promoter, operably associated with a nucleic acid sequence expressing a product of interest, initiates and regulates the transcription of such sequence in a root-specific manner.

According to another aspect of the present invention, an isolated DNA sequence from position −1687 to +69 of the sequence illustrated in FIG. 1, and which drives transcription of a downstream endogeneous or heterologous DNA segment in plant cells, or a DNA sequence which is a functionally equivalent variant thereof, is provided.

According to a further aspect of the invention, a plant root-specific promoter which has a nucleotide sequence of from position −1687 to +69 of the sequence illustrated in FIG. 1, or a functionally equivalent variant thereof, is also provided.

According to yet another aspect of the invention, a DNA construct which comprises:
(a) a promoter sequence as defined above;
(b) an open reading frame polynucleotide coding for a polypeptide; and
(c) a terminal sequence, is provided.

In each construct the open reading frame is in a sense orientation, or an anti-sense orientation.

In each construct, the open reading frame can be in a 5' to 3' orientation, or in a 3' to 5' orientation.

In one embodiment, the open reading frame encodes a polypeptide having the sequence illustrated in FIG. 1 (SEQ ID No. 24).

In another embodiment, the open reading frame encodes a polypeptide which, when expressed in root tissue of a plant, results in a useful trait in said plant.

In a further embodiment, the construct further includes a selection marker sequence e.g. the NPTII gene.

In yet another embodiment of the invention, a transgenic plant cell which includes a construct as described above, is provided. By "transgenic" used herein is meant containing genetic material which is either does not occur naturally in the wild-type plant cells of that type, or which occurs naturally only in a different location in the genome.

In a further embodiment, the invention provides a transgenic plant, which includes a construct as described above.

In yet a further embodiment, the invention provides transgenic plants, which contain a DNA sequence having activity as a functional promoter as described above or a root-specific promoter as described above, which plant has a new and useful trait in its root tissue.

Conveniently, in said plant the said DNA sequence or promoter is operatively associated with a nucleotide sequence encoding a heterogeneous protein.

The plant can be a species of angiosperm plants or gymnosperm plants. The plant may be a member of a species selected from dicots and monocots.

For example, the plant can be a coniferous plant, such as a coniferous plant of the Pinus genus. The coniferous plant may be a member of a species selected from *Pinus radiata, Pinus taeda, Pinus elliotti, Pinus clausa, Pinus palustrus, Pinus echinata, Pinus ponderosa, Pinus jeffrey, Pinus resinosa, Pinus rigida, Pinus banksiana, Pinus serotina, Pinus strobus, Pinus monticola, Pinus lambertiana, Pinus virginiana, Pinus contorta, Pinus cariboea, Pinus pinaster, Pinus brutia, Pinus eldarica, Pinus coulteri, Pinus nigra, Pinus sylvestris, Pinus tecunumannii, Pinus keysia, Pinus oocarpa* and *Pinus maxinumoii*; and hybrids between any of the above species.

The plant may be a tree.

BRIEF DESCRIPTION OF THE DRAWINGS

FIG. 1 is a depiction of the nucleotide sequence of PmPR10-1.14 gene and flanking regions (SEQ.ID.NO. 20). Nucleotides are numbered on the left side, with the position corresponding to the first nucleotide of cDNA designated as +1. Amino acids are numbered on the right side. Two highly conserved direct repeats are underlined.

DETAILED DESCRIPTION OF THE INVENTION

Figure 2:
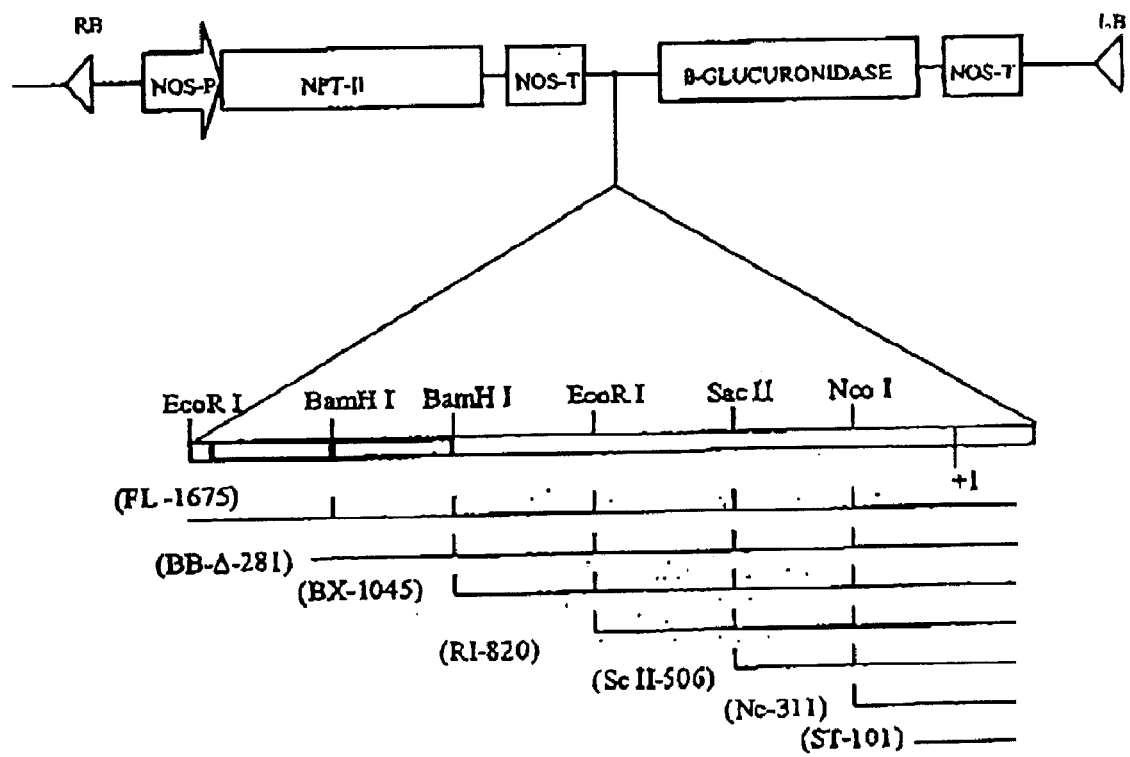
FIG. 2. is a chematic representation of different PmPR10-1.14::GUS fusions. The promoter fragments (FL to ST) were inserted into pBI101 to construct plant gene expression vectors. The length of the promoter deletion, the positions of restriction enzyme sites used for vector construction are indicated schematically. Position (+1) is corresponding to the first nucleotide of PR10 cDNA. The DNA and amino acid sequences are shown to describe the fusion of uidA gene to PmPR10-1.14 promoter. Codons in lower-case letters are derived from the sequence of pBI101.

There is provided a plant promoter which directs gene expression in a root-specific manner. The promoter, which was isolated from *Pinus monticola,* is described herein as the "PmPR 10-1.14 promoter". The nucleotide sequence of the PmPR10-1.14 promoter is given in SEQ. ID. NO. 1 from nucleotide −1678 to +69 relative to the first nucleotide of its corresponding cDNA. It will however be appreciated that the invention is not restricted only to polynucleotides having that specific nucleotide sequence. Instead, the invention also extends to variants of such polynucleotides.

As used herein, a "variant" of the PmPR10-1.14 promoter polynucleotide sequence or any portion thereof is any sequence of at least 100 nucleotides (which may include non-natural and/or modified nucleotides) which, when situated upstream of a reporter sequence which is expressible in tobacco and functionally incorporated into root cells in tobacco, directs root-preferential or root-specific expression of the reporter sequence in tobacco. In some instances, the variant contains a continuous polynucleotide sequence of at least 100 nucleolides which has at least 90% homology to a 100 nucleotide long region contained within the PmPR10-1.14 promoter between positions −101 and +69 (SEQ ID No. 2) as described herein. In some instances, the variant contains a continuous polynucleotide sequence of at least 150 nucleotides which is at least 70% homologous to a sequence of the same length in the PmPR10-1.14 promoter sequence between position −101 and +69 (SEQ ID No. 2) as described herein. In some instances, the variant contains a continuous polynucleotide sequence of at least 150 nucleotides which is at least 80% homologous to a sequence of the same length in the PmPR10-1.14 promoter sequence between position −101 and +69 (SEQ ID No. 2) as described herein. In some instances, the variant contains a continuous polynucleotide sequence of at least 150 nucleotides which is at least 90% homologous to a sequence of the same length in the PmPR10-1.14 promoter sequence between position −101 and +69 (SEQ ID No. 2) as described herein. In some instances, the variant contains between 150 and 1750 nucleotides. In some instances, the variant contains a continuous polynucleotide sequence of between 1500 and 1750 nucleotides which is at least 60% homologous to the PmPR10-1.14 sequence between positions −1675 and +69 (SEQ ID No. 1) as described herein. In some instances, the variant contains a continuous polynucleotide sequence of between 1500 and 1750 nucleotides which is at least 70% homologous to the PmPR10-1.14 sequence between positions −1675 and +69 (SEQ ID No. 1) as described herein. In some instances, the variant contains a continuous polynucleotide sequence of between 1500 and 1750 nucleotides which is at least 80% homologous to the PmPR10-1.14 sequence between positions −1675 and +69 (SEQ ID No. 1) as described herein. In some instances, the variant contains between 1500 and 1750 nucleotides which is least 90% homologous to the PmPR10-1.14 sequence between positions −1675 and +69 (SEQ ID No. 1) as described herein.

A variant will in some instances hybridize under stringent conditions to the complementary strand of the polynucleotide of which it is a variant. Stringent conditions for hybridisation are prehybridizing in a solution of 6×SSC, 0.2% SDS; hybridizing at 65° C., 6×SSC, 0.2% SDS overnight; followed by two washes of 30 min each in 1×SSC, 0.1% SDS at 65° C. and two wash washes of 30 min each in 0.2×SSC, 0.1% SDS at 65° C.

It is expressly contemplated that homologs of PmPR10-1.14 promoter exist in other plants (including other coniferous plants, including other members of Pintis genus) which are homologous to the core promoter sequence of PmPR10-1.14 from −101 to +69 (SEQ ID No. 2), or from −311 to +69 (SEQ ID No. 7). Such a homologue may be a variant of the PmPR10-1.14 promoter sequence, if it is a sequence of at least 100 nucleotides which, when situated upstream of a reporter sequence which is expressible in tobacco and stably incorporated into the tobacco genome, directs root-preferential or root-specific expression of the reporter sequence in tobacco.

As described herein, a "modified nucleotide" is any nucleotide other than adenine, guanine, cytosine, thymine and uracil which can be incorporated into a polynucleotide sequence By way of non-limiting example, modified nucleotides include: inosine, any nucleotides derived from Adenine(A), Guanine (G), Cytosine (C), Thymine (T), Uracil (U), or inosine by chemical modification (for example by adding chemical group(s) for detection), 4-acetylcytidine, 5-(carboxyhydroxymethyl) uridine, 2'-O-methylcytidine, 5-carboxymethylaminomethyl-2-thiouridine, 5-carboxymethylaminomethyluridine, dihydrouridine, 2'-O-methylpseudouridine, beta, D-galactosylqueuosinie, 2'-O-methylguanosine, inosine, N6-isopentenyladenosine, 1-methyladenosine, 1-methylpseudouridine, 1-methylguanosine, l-methylinosine, 2,2-dimethylguanosine, 2-methyladenosine, 2-methylguanosine, 3-methylcytidine, 5-methylcytidine, N6-methyladenosine, 7-methylguanosine, 5 methylaininomethyluridine, 5-methoxyaminomethyl-2-thiouridine, beta, D-mannosylqueuosine, 5-methoxycarbonylmethyl-2-thiouridine, 5-methoxycarbonylmethyluridine, 5-methoxyuridine, 2-methylthio-N6-isopentenyladenosine, N-((9-beta-D-ribofuranosyl-2-methylthiopurine-6-yl)carbamoyl)threonine, N-((9-beta-D-ribofuranosylpurine-6-yl) N-methylcarbamoyl)threonine, uridine-5-oxyacetic acid-methylester, uridine-5-oxyacetic acid, wybutoxosine, pseudouridine, queuosine, 2-thiocytidine, 5-methyl-2-thiouridine, 2-thiouridine, 4-thiouridine, 5-methyluridine, N-((9-beta-D-ribofuranosylpurine-6-yl)-carbamoyl)threonine, 2'-O-methyl-5-methyluridine, 2'-O-methyluridine, wybutosine, 3-(3-amino-3-carboxy-propyl)uridine, (acp3)u.

As used herein, the term "root preferential" gene expression refers to expression of the gene in the root at levels at least 15 times higher than the average level observed in leaves and stem. As used herein, the term "root specific" gene expression refers to expression of the gene in the root at levels at least 35 times higher than in leaves and stem (average).

A surprising feature of PmPR10-1.14 promoter structure is that it contains many Dof cis-elements and TAACAAA-like boxes (Table I). Dof cis-elements are the binding sites of Dof proteins, involving in a variety of signal-responsive and/or tissue-specific gene expressions in plants. The Dof cis-element in the promoter of a oncogene (rolB) in tobacco acts as a transcriptional regulatory motif and is essential for tissue-specific and auxin-regulated expression in primary root apex, secondary root primordium and shoot apical meristem, respectively. TAACAAA-like boxes are the binding sites of a class of transcription factor GAMYB, which is responsible for the tissue-specific expression of GA-regulated genes in cereal aleurone cells. These GA-regulated genes encode hydrolytic enzymes including α-axnylases, α-glucosidase, (1-3, 1-4)-β-glucanase, proteases, (1-4)-β-xylan endohydrolase and nucleases, which are responsible for the digestion of the stored nutrients in the endosperm. As used herein, the term "Dof element" refers to the nucleotide sequence NNNWAAAGNNN, wherein N is A, G, C, or T and W is A or T (SEQ.D.NO. 23).

As used herein, the term "Dof element" refers to the nucleotide sequence 5'NNNWAAGNNN, wherein N is A, T, G or C and W is A or T (SEQ.ID.NO.23), or to the inverted form thereof (5'NNNCTTTWNNN).

Some of the Dof elements in the promoter are inverted.

Figure 1:
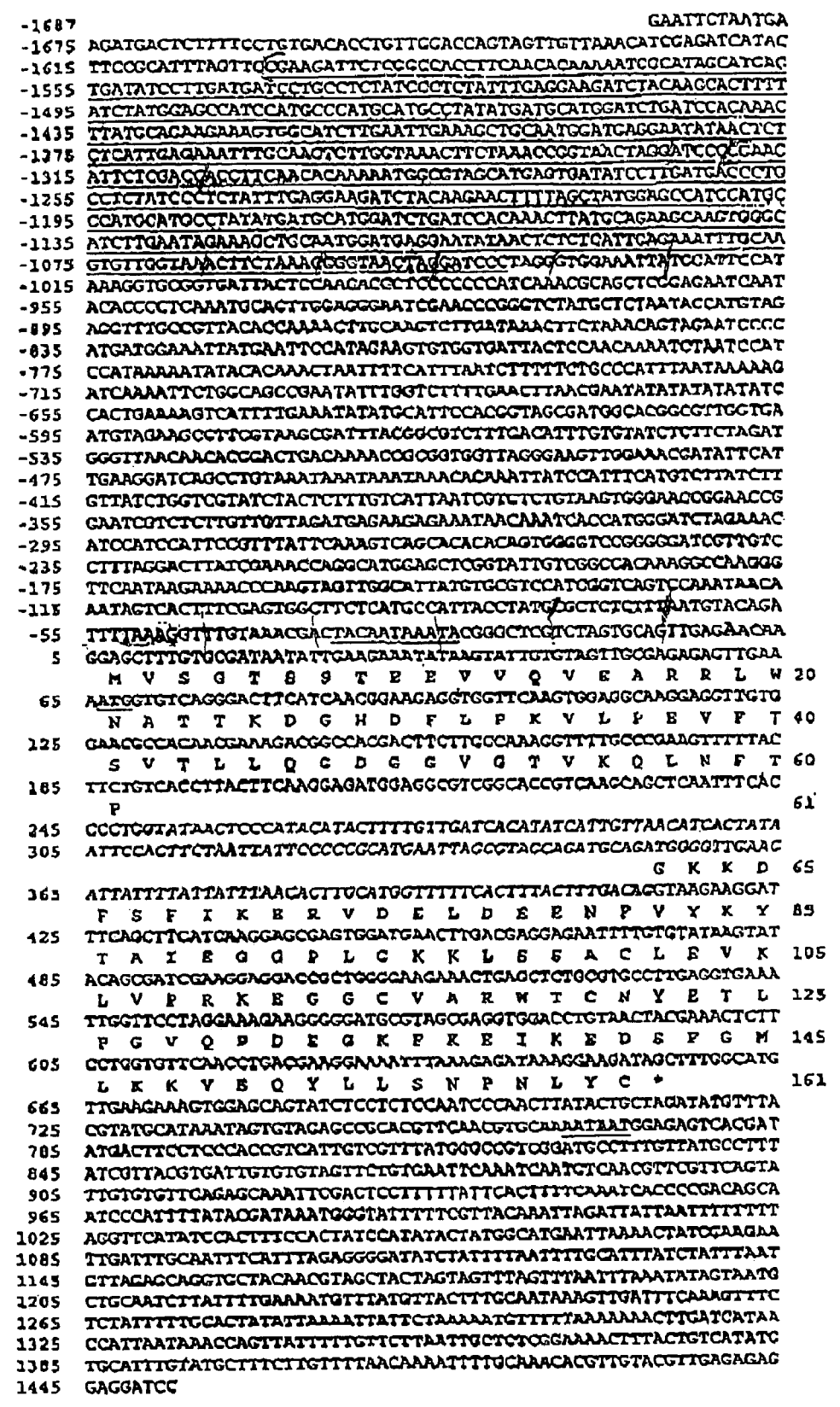

The nucleotide frequency matrix for the TATA box in plant promoters is shown in Table IV. As used herein the term "TATA box" refers to the nucleotide sequence (T/A/C) (A/T) (T/C) A (A/T) (A/G/T) (T/A/C) N; wherein N can be any one of A, T, G or C. In some instances a TATA box having the sequence TATA(A/T)A(T/A)A will be desired. In some instances, a TATA box having the sequence TACAATAAATA will be desired. In some instances a TATA box having the sequence TATAATAAATAG will be desired. In some instances a TATA box having the sequence TACAATAAG will be desired. In some instances a TATA box having the sequence TACATAATA will be desired. In some instances a TATA box having the sequence TACAATTAA will be desired. It will be understood by those skilled in the art, in light of the disclosure herein, that a variety of TATA box sequences are contemplated and it is not intend to limit the invention to the specific examples. In light of the disclosure herein, one skilled in the art could select a suitable TATA box sequence for use in a particular plant species The generation and subsequent analysis of a series of 5' deletions of the PmPR10-1.14 gene were performed to identify regions responsible for mediating the gene expression pattern (Table III). The analysis of transient gene expression in agroinfiltrated tobacco leaves identified the core promoter of PmPR10-1.14 gene as the sequence from −101 to +69 (SEQ.ID. NO.2). The gene sequence from −101 to +69 contains one putative TATA box-like element at −34 bp, two Dof cis-elements at −72 and −55, plus 5'-untranslated region, which may serve as the cis-regulatory elements for the basic gene expression. In some instances it will be desirable to reorientate Dof elements so as to invert or un-invert them relative to the rest of the promoter sequence. For example, in FIG. 1, the Dof element at position −72 is inverted whereas the Dof element at position −55 is not inverted. 5'-deletions of the PmPR10-1.14 gene from−1675 to −506 were found to have no obvious effects on transient gene expression. But a further deletion to −311 was shown to drive gene expression at an increased level of 3 to 4 times higher in agroinifiltrated tobacco leaves (FIG. 3), suggesting the enhancer element(s) reside in the region from −311 to −101, and silencer element(s) in the sequence from −506 to −311.

Figure 8:
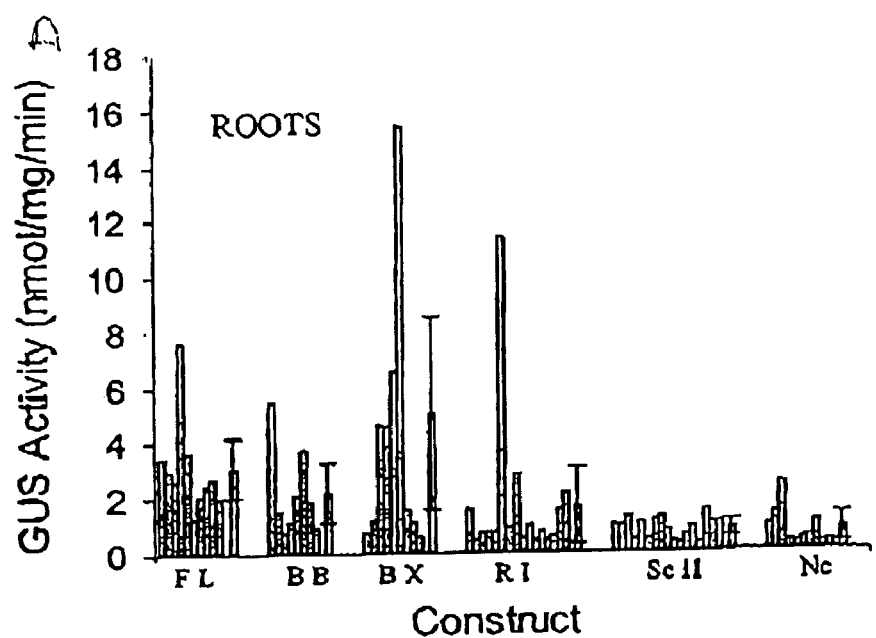
FIG. 8 is a graphical depiction of the effect of 5' deletion on GUS expression in leaves (B) and rooLs (A) of *N. tabacum* transformed with various PmPR10-1.14::GUS fusions. Each gray bar represents the value of a transgenic line, white bar represent the mean value ± deviation of the mean. The increased GUS activities in plants harboring constructs BB-▲-281 and BX-1045 are statistically significant (P<0.031 and P<0.014, respectively), indicated with "*". The black tiangle is a symbol, indicating that in this vector (BB-black triangle-281) a repeat sequence of 281 bp was deleted. Statistical analyses show no significant differences of GUS expression in roots among different constructs.
Figure 8:
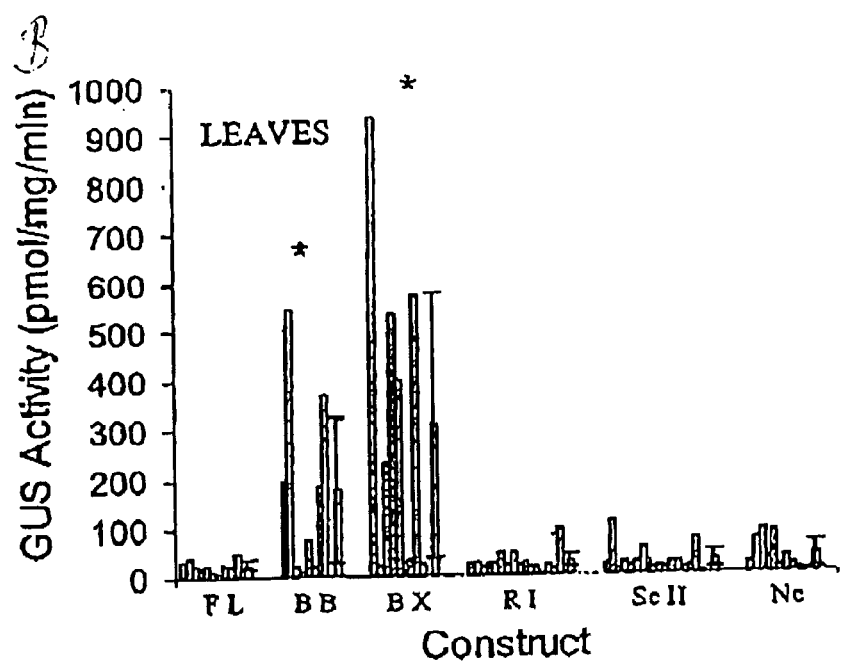
Figure 9:
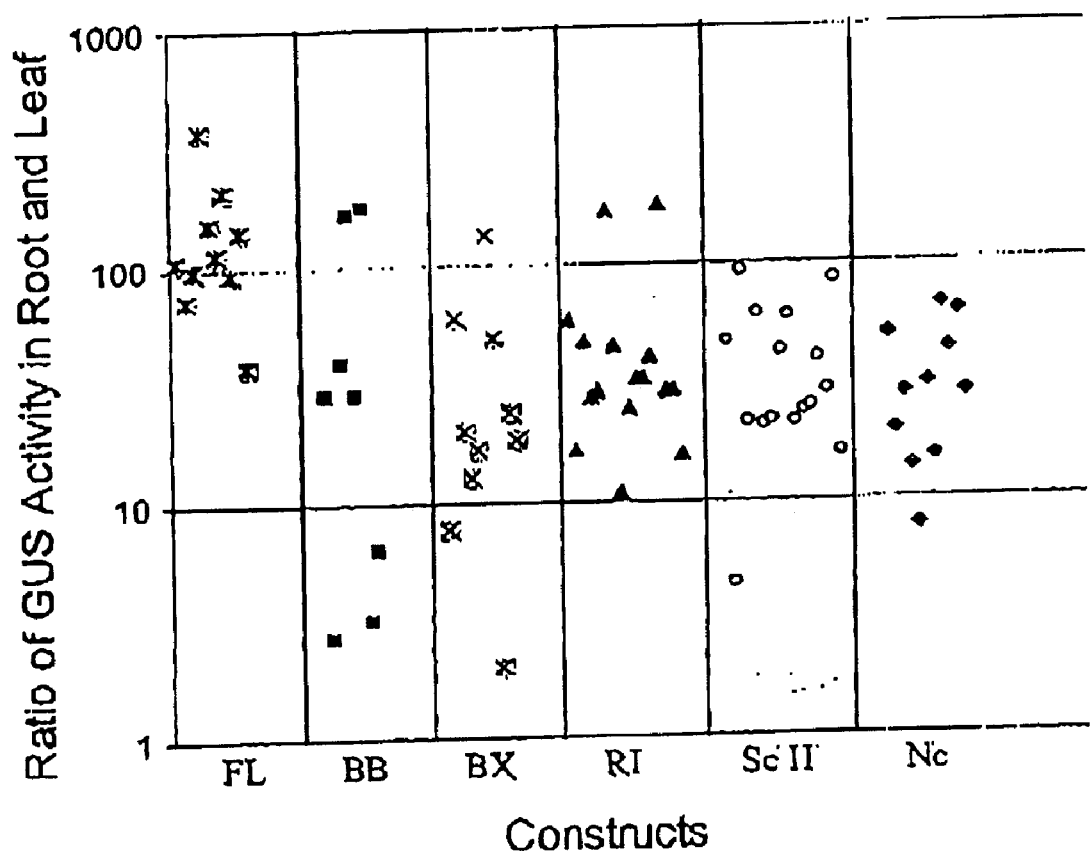
FIG. 9 is a depiction of the relative GUS activity observed in roots and leaves of tobacco plants transformed with chimeric reporter gene constructs using different promoter fragments. The ratio of root GUS activity/leaf GUS activity is determined for individual T1 transgenic lines with different promoter deletions.

The level of GUS activity measured in the roots of transgenic plants harboring −311 promoter (SEQ. ID. NO. 7) was not significantly different from that produced in root tissues of transgenic plants containing the −1675 bp promoter (SEQ. ID. NO. 1) of PmPR10-1.14 gene. 5′-deletion of the promoter to −311 still drove gene expression at high levels in roots (FIG. 8). Thus, positive cis-regulatory elements that drive the constitutive expression of PmPR10-1.14 gene in roots of transgenic tobacco reside between −311 to +69. When the ratio of GUS activity in roots to that in leaves is analyzed, the ratio established by the −311 bp promoter in construct Nc was about one-third of that observed for the −1675 hp promoter in construct FL (FIG. 9) and this change was gradual as the deleted region grew. Therefore, some positive quantitative elements responsible for root-specific expression may be located between −1675 to −311.

There are two TAACAA-like boxes for GAMYB binding and one Dof cis-element at position −398 in an inverse orientation in the context from −506 to −311 (Table 1). The cis-elements associated with TAACAA-like box appear to be analogous to enhancer elements in angiosperms. In maize Dof1 is a transcription activator which shows different activity in greening and etiolated protoplasts, whilst Dof2 is expressed mainly in stems and roots with both positive and negative effects on promoters in different contexts. One silencer motif for the binding of trans-factor SBF1 is located at position −538 (Table I), and is therefore unlikely to be responsible for the negative effect of the sequence from −506 to −311. Enhancer or activator elements dramatically increase the transcriptional activity of certain plant genes. The promoter region from position −311 to −101 is rich in various cis-element: one CAAT box at position −173, four Dof cis-elements at position −110,−191, −238,−278, and one CAACAAA-like box at position −245, and one cis-element for the binding of bZIP910 at position −273. It is noteworthy that the potential binding sites for bZIP910 (−273) and one Dof protein (−278) are close to each other in the promoter region of PmPR10-1.14 gene, suggesting that there might be interaction of different transcription factors. In the promoters of seed storage protein α-zein genes, the cis-elements for the binding of a Dof protein PBF and a bZIP protein O2 are closely located and responsive for endosperm-specific gene expression. In the promoter of Arabidopsis glutathione S-transferase (GST) gene the binding sites for a Dof protein OBP1 and a bZIP protein OBF are also close to each other, and the interaction of OBP1 with OBF enhance the binding of OBF to Dof cis-element (Zhang et al., 1995). Therefore, the presence and interaction of these putative cis-elements may be a significant factor for the gene expression at high levels in the transient expression assays and in the roots of transgenic plants.

An unusual feature of PmPR10-1.14 promoter is the presence of two copies of repeated sequences at its 5′-distal region (FIG. 1). Surprisingly, stable transformation experiments showed that removal of one copy (−1326 to −1045) or both copies (−1675 to −1045) of these repeated sequence results in significantly increased expression levels in the leaves (FIG. 8) and stems, but not in other tissues. When the progressive 5′-deletion went from −1045 to −820, the increased GUS gene expression in leaves and stem was abolished (FIG. 8). Thus, it appeared that both enhancer and silencer elements were functioning in the leaves and stems. The silencer element is believed to be located in the repeated sequences, and enhancer element in the region from −1045 to −820 (nucleotides 642 to 867 in SEQ.ID.NO.20). There are two Dof cis-elements and one CAATAAA element in the repeated sequence, but these elements or unidentified element do not seem to, individually, relate to the increased expression in leaves and stems (as there is no difference between deletion of one copy and two copies of the repeated sequence). This type of long repeated sequence has the ability to form stable secondary structures, (e.g. hairpin structures) and possibly to provide a potential binding site for regulatory proteins.

Thus, leaf and/or stem expression can be reduced using a polynucleotide sequence useful in reducing expression of a downstream gene said polynucleotide sequence comprising two copies of a DNA region each being independently at least 70%, 80% or 90% homologous to a region of substantially equal length containing at least 150 nucleotides (preferably at least 200 nucleotides, more preferably at least 250 nucleotides) contained between nucleotides −1326 and −1048 of SEQ.ID.NO. 20 as depicted in FIG. 1 (nucleotides 361 to 639 as numbered in SEQ.ID.NO 1), said copies being separated by between 0 and 100 nucleotides. In some cases the two copies have the same sequence. In some instances the copies are separated by between 0 and 50 nucleotides. In some instances the copies are separated by between 0 and 20 nucleotides.

Thus, leaf and/or stem expression can be increased using a polynucleotide sequence at least 70%, 80% or 90% homologous to a continuous nucleotide sequence of at least 150 nucleotides (preferably 200 nucleotides) located between nucleotide −1045 and −820 of SEQ.ID.NO. 20, as numbered in FIG. 1.

There are provided modulators of gene expression. In some instances these modulators comprise a polynucleotide sequence of at least 100 nucleotides which is at least 70% homologous to a continuous 100 bp stretch of SEQ.ID.NO. 21 or 22 or a variant thereof. In some instances, modulators of gene expression are at least 150 bp long. In some instances modulators of gene expression are at least 80% homologous to one of SEQ.ID.NO. 21 or 22 or a variant thereof. In some instances modulators of gene expression are at least 90% homologous to one of SEQ.ID.NO. 21 or 22. In some instances modulators at gene expression are at least 95% homologous to one of SEQ.ID.NO. 21 or 22. In some instances a modulator of gene expression is a variant of SEQ.ID.NO. 21 or 22. In some instances, modulators of gene expression are between 100 and 200 bp long.

TABLE III

| Promoter Region | Functional Activity | SEQ. ID. NO. |
| --- | --- | --- |
| −1675 to +69 | Root-specific expression with enhanced effect | SEQ. ID. NO. 1 |
| Deletion from −1600 to −1039 or from −1326 to −1048 | Increased expression in leaf and stem | SEQ. ID. NO. 3<br>SEQ.ID.NO. 19 |
| −1045 to +69 | Increased expression in leaf and stem | SEQ. ID. NO. 4 |
| −820 to +69 | Root-specific expression | SEQ. ID. NO. 5 |
| −506 to +69 | Root-specific expression | SEQ. ID. NO. 6 |
| −311 to +69 | Root-specific expression | SEQ. ID. NO. 7 |
| −101 to +69 | Core promoter region | SEQ. ID. NO. 2 |
| −506 to −311 | Neg.cis.reg. elements | SEQ. ID. NO. 22 |
| −311 to −101 | Pos.cis-reg. elements | SEQ. ID. NO. 21 |

Thus, there is provided an isolated and characterized a western white pine PR10 gene and a plant promoter suitable to drive gene expression in a root-preferential and/or root-specific manner in transgenic plants. Root specific promoters are of special interest because of physiological functions in root, and the root's vulnerability to attack by pathogens and pest. The PmPR10-1.14 promoter and variants thereof offer a wide range of applications in industry to express endogenous or foreign proteins in roots to enhance plant resistance to pathogens and pests; stress tolerance to heat, salt or drought; and to improve nutritive value of edible root plants; and production of recombinant proteins aimed at molecular farming and phytoremediation.

In some instances it will be desirable to produce transgenic plants or cells, tissues, parts or seeds thereof including a transiently or stably incorporated root-specific promoter and a gene of interest.

A gene of interest may be any gene which encodes a product useful in the root. For example, genes encoding antifungal peptides such as luffacylin, ascalin, and Western white pine 10 kDa protein may be of interest. Similarly, genes related to nitrogen fixation or other nutritional elements may be of interest, including: nitrate transporter proteins, nitrate reductase, nitrite reductase, glutamate synthase, and ammonium transporter proteins. In some instances, genes encoding pest-deterrents such as compounds toxic or unpalatable to insects may be desired. In some instances, the gene of interest may encode a peptide or protein which is an antigen in mammals and is useful as a vaccine. In some instances the antigen will be selected to be useful as a vaccine when orally administered.

Thus it will be apparent that there has been provided a promoter suitable for use in plant cells.

Example 1

Plant Materials

Seedlings of western white pine (*Punus monticola* Dougl. Ex D.Don) were grown under natural conditions in the green house, or in the growth chamber maintained for a 16-h day (24° C.) and an 8-h night (20° C.) under light illumination (2000 lux). The developing male cones and female cones were collected from mature trees in May 2000 at Pacific Forestry Centre, Victoria, BC, Canada. Tobacco plants (*Nicotiana tabacum* cv. ws38) were grown in growth chambers for agoinfiltration and gene transformation.

Example 2

PR10 Gene Cloning and PCR Amplification

Genomic DNA was isolated from needles of current year of western white pine using a DNA easy kit (Qeagene). A two-step PCR strategy was used for the genomic DNA cloning of PR10 genes in western white pine. First, the inverse polymerase chain reaction (IPCR) was performed to clone the flanking sequences of coding region. The reverse primer GSP1 (5'-CCT TGC CTC CAC TTG AAC CAC CTC TTC CG-3' SEQ.ID.NO.8) and forward primer 3SE1 (5'-C CTC TCC AAT CCC AAC TTA TAC TG-3' SEQ.ID.NO.9) used in IPCR hybridize to the sense and antisense strands of the PR 10 cDNA of Pin m III (Yu etal., 2000), respectively. Second, a pair of primers were designed based on the flanking sequences obtained above to perform long distance PCR to clone the whole PR10 gene, including promoter region, coding region and down stream region after stop codon. The primers used in long distance PCR for the genomic DNA cloning of full-length PR10 gene were forward primer B43-5' (5'-AA <u>AAGCTT CTCGAG</u> ATG ACT CTT TTC CTG TGA CAC-3'SEQ.ID.NO.10) and reverse primer BG3 (5'-CAT CGG ATA GTA TAT GGA TAG TGG-3'SEQ.ID.NO.11). 1.5 µg of genomic DNA was digested with appropriate restriction enzymes (BamH I or EcoR I), then circularized using T4 DNA ligase. The IPCR was performed using 100 ng of re-circularized genomic DNA as template in final volume of 50 µl. PCR was carried out with an Advantage Genomic PCR Kit (Clontech Laboratories, Inc. CA, USA) using a Perkin-Elmer Themocycler. Thermal cycling conditions consisted of an initial denaturation step at 94° C. for 3 min, followed by thirty cycles of denaturation at 94° C. for 30 sec, and primer annealing and extension at 68° C. for 5 min, with a final 10-min extension at 72° C. PCR products were cloned into pGEM-T easy vector (Promega, WI, USA), and plasmid constructions and manipulation were carried out using standard methods (Sambrook et al., 1989). DNA sequence were determined on both strands with ABI310 DNA sequencer (Applied Diosystem) using Thermoycle sequence kit (Amersham) with T7, SP6 primer and other internal primers as needed. DNA sequence data were assembled and analyzed using BLAST, CLASTOW and ORF finder network services at the National Center for Biotechnology Information (NCBI).

Example 3

RNA Isolation and Analysis

Total RNA was isolated according to the method of Liu et al. (1998) with some modifications. Briefly, total RNA was extracted from western white pine tissues after treatments. Each sample (~0.5 to 1.0 g) was ground to a fine powder in liquid nitrogen, then homogenized in 10 mL of extraction buffer (0.1 M Tris-HCl, pH7.4, 50 mM EDTA, 0.5 M NaCl, 2% SDS, 2% PVP, and 10 mM β-mercaptoethanol). The mixture was incubated for 20 min at 65° C. Cellular debris was removed by centrifugation of 12,000 g for 15 min at room temperature. To the supernatant, 3.3 mL of 5 M Kac (pH5.5) was added. The mixture was incubated on ice for 30 min, then centrifuged at 12,000 g for 10 min at 4° C. After phenol/chloroform extraction, the RNA was precipitated from supernatant by adding ⅓ volume of 8 M LiCl and incubating overnight at 4° C. The RNA was recovered by centrifugation at 12,000 g for 30 min, and washed with 2 M LiCl and 70% ethanol. The air-dried RNA precipitate was re-suspended in 50 µL of TE buffer (10 mM Tris-HCl, pH 7.5, 1 mM EDTA) and kept at −80° C. until use. The RNA concentration of individual extracts was determined by UV absorbency and the integrity was checked by agarose gel electrophoresis and ethidium bromide staining. There was some genomic DNA in die isolated total RNA, which was removed by LiCl precipitation. 10 µg of total RNA was then electrophoresed in a denaturing agrose gel and blotted onto nylon membranes (Hybond-N+, Amersham). A probe was labeled with digoxygenin (DIG) using a random primer labeling kit (Boehringer Mannheim), used to hybridize to the 3'-untranslated region of PR10 gene. Hybridizations were performed at 65° C. in a hybridization buffer (0.5M Na PO₄. pH8.0, 7% SDS, 1 mM EDTA). Blots were washed finally in 0.1×SSC and 0.1% SDS at 65° C. The membranes were exposed to X-ray film for autoradiography.

Example 4

Protein Extraction and Western Immunoblot Analyses

Total proteins were extracted from tissues of western white pine (Ekramoddoullah and Hunt 1993). Briefly, 50 to 100 mg of tissue powder was mixed with extraction buffer#1 (4% SDS, 5% sucrose, 5% mercaptoethanol). After vortexing for 30 min, the sample tubes were immersed in boiled water for 6 min, and vortexed for an additional 30 min. After centrifuging at 14,000 rpm for 10 min, 8× cold acetone was added to supernatant, mixed well and incubated at −20° C. for at least 1 hour. Then the protein pellet was spinned down at 14,000 rpm for 10 min and dried in fume hood. 50 µl of extraction buffer #2 (4% SDS, 5% sucrose, 1% NP-40) was added to the dried protein pellets. To resuspend the protein pellet completely the pellet was heated in boiled water for 3 to 5 min. After centrifuging at 14,000 rpm for 10 min, the supernatant of protein solution was recovered and stored at −20° C.

The protein samples were separated by SDS-ployacrylainide gel electrophoresis (PAGE), or two-dimensional PAGE, and transferred onto nitrocellulose membrane. For immunodetection, the blots were incubated with polyclonal antibodies against a PR10 protein (Pin 1 I) from sugar pine as described by Ekramoddoullah, et al (1995). The scanning, detection and quantitation of the blots were performed with PDI Quantity One software (Version 3.0, PDI, Huntington Station, N.Y., USA) according to the PDI instruction manual. The protein level detected by western immunoblot analyses was calculated based on the optical density (OD) of all pixels within the band boundary, and expressed in OD units×millimeter.

Example 5

Constructs for Promoter Analyses

To construct binary vectors, PCR was used to introduce appropriate restriction enzyme sites at both 5'- and 3'-ends of the promoter sequence of the PmPR10-1.14 gene with the forward primer B43-5 (SEQ.ID.NO.10) and a reverse primer PBS (5'-AA GGATCC GTCGAC CAT TTT CAA CTC TCT CGC AAC-3'SEQ.ID.NO.12). Primer B43-5 was incorporated with synthetic Hind III/Xho I restriction enzyme sites at its 5'-end. BamH I/Sal I restriction enzyme sites were introduced at positions followed start codon (ATG) of coding region in primer PBS. The promoter fragment was cloned into pGEM-T easy vector. A series of 5'-deletions were made with double restriction enzyme digestion of Xho I combined with BamH I, EcoR I, Sac II, or Nco I to obtain the promoter deletion at positions −1045 (BX), −820 (RI), −506 (Sc II), and −311 (Nc), respectively. Single enzyme digestion of BamH I was used to delete one copy of 281 bp repeated sequence to obtain promoter deletion BB-Δ-281. The deletion of PmPR10-1.14 gene to −101 (ST) was made using PCR with primer PBS and an additional forward primer B-101 (5'-AAAAGCTTA GTG GCT TCT CAT GCC AT-3'SEQ.ID.NO.13). All deletions were verified by DNA sequencing analysis. Hind III/Sal I digested promoter fragments were inserted into the polylinker Hind III/Sal I sites of pBI101 vector (Jefferson et al., 1987; Clontech Laboratories, CA, USA), resulting in chimeric constructs FL (−1675), BB (-Δ-281), BX (−1045), RI (−820), Sc II (−506), Nc (−311), and ST (−101), respectively (FIG. 2).

Example 6

Agroinfiltration and Stable Transformation of Tobacco Plants

Plasmid DNA of binary constructs were introduced into *Agrobacterium tumefaciens* (LBA 4404) with a freeze-thaw method. The transient gene expression using agroinfiltration was performed following the procedure as described by Yang et al. (2000).

For stable gene expression, tobacco plants were co-cultivated with *Agrobacterium* by the standard leaf disc-infection method (Horsch et al., 1985). Briefly, a single colony of the *A. tunefaciens* strain containing corresponding binary vector from a fresh plate was inoculated in a 10 ml culture in 2×YT liquid media supplemented with 50 µg/ml kanamycin and 25 µg/ml genetamycin. The culture grew overnight at 28° C. with shaking until the culture reach late logarithmic phase ($A_{600}$ of ~0.8). After spinning down at 5000 g for 10 min, the *Agrobacterium* was washed and resuspended in MS medium. Young leaves were removed from sterile tobacco plants and cut into leaf disk with size about 3×4 mm. The leaf disks were soaked in the resuspended *Agrobacterium* solution, then transferred upside down onto petri dish plates of MS media. After co-culture of *Agrobacterium* and leaf disks for two days at 22° C., the leaf disks wee transferred onto MS selection media and incubated at 22° C. with a 16h-day length at light intensity of 3000 lux for about a few weeks. When shoots grew to 1-2 cm, they transferred into megenta pots containing rooting media. Shoot segments with roots and leaves developed in 3-4 weeks, then were transferred into soil.

Transformants were selected on Murasgige and Skoog's medium supplemented with 200 µg/mL kanamycin and 500 µg/ml carbenicillin. Regenerated plants were analyzed for the integration of the promoter-uidA fusion genes into plant genome by PCR. The forward primer (BI-For) was synthesized on the sequence upstream the polylinker region of vector pBI-101 (5'-ACA CAG GAA ACA GCT ATG ACC ATG-3'SEQ.ID.NO.14). The reverse primer was PBS previously used for binary vector construction, or primer BI-Rev (5'-GGT TTC TAC AGG ACG TAA CAT AAG-3'SEQ.ID.NO.15). Hundreds of independently transgenic lines were selected as representative of promoter-directed gene expression. Kanamiiycin-resistant transformants of these lines were grown in soil in controlled environmental chamber with conditions mentioned above. Primary transgenic plants and progeny were referred to as T1 and T2 plants, respectively.

To determine GUS activity of the primary transgenic plants, different tissue samples were collected from each transgenic line about two months after plantlets were removed into soil from Murashige-Skoog selection medium. Roots were washed carefully to remove any soil, and taken from various parts of the root bale as root samples. Leaf samples were collected from the young leaves just full expansion about the third from the top; and stem samples collected around the same position as the leaf samples. Flower organs were collected just one day before flower open. For experiments with T2 seedling, seeds from T1 generation were germinated under sterile condition and selected on Murashige-Skoog medium supplemented with 10 g/L sucrose and 400 µg/mL of kanamycin, and grown in a sterile environment with conditions mentioned above. At times indicated in the figure legends, the samples of roots, stems and leaves, or whole seedlings were collected for GUS activity assays.

Example 7

Fluorometric and Histochemical GUS Assays

Fluorometric GUS assays of crude plant extracts were performed as described by Jefferson (1987). Briefly, tissue samples were collected in 1.5 mL Eppendorf tube and ground in 450 µL GUS extraction buffer (50 mM $NaPO_4$, pH 7.0, 10 mM EDTA, 0.1% [v/v] Triton X-100, 0.1% Sarkosal, 10 mM β-mercaptoethanol). After centrifugation of 12,000 ×g for 10 min at 4° C., 50 µL of the supernatant of crude extract was mixed with 1 mM 4-methylumbelliferyl glucuronide (4-MUG) in 0.45 mL of extraction buffer. At time 0-h and 1-h of incubation at 37° C., 50-μL aliquots were removed and mixed with 2 mL of stop solution (0.2 M $Na_2CO_3$) to terminate reaction. GUS activity was determined with a DyNAQuant 200 fluorometer (Hoefer, Calif., USA), and protein concentration of crude extracts was determined with a method as described previously (Ekramoddoullah and Davidson 1995). Briefly, after dilution in protein extraction buffer #2 when it was necessary, 1 μl of protein extracts was spotted on a PDVF membrane. 1 μl of BSA from concentration from 0.1 to 1.0 μg/μl was used as standard. The membrane was air-dried and stained for 10 min with 0.1% Coomassie Blue in 50% methanol/water, then distained in 10% acetic acid/50% methanol/40% water. Membrane was scanned and protein concentration was determined by Quantity-One software from BioRad.

Histochemical localization of β-glucuronidase activity was performed essentially as described by Jefferson (1987) with 5-bromo-4-chloro-3-indolyl-β-glucuranide (X-Gluc, Clontech, CA, USA) as a substrate.

Transgenic samples were vacuum infiltrated for a few minutes with 1 mM X-Glu in 50 mM sodium phosphate, pH7.0, 0.02% Triton X-100 and 0.5 mM each of $K_3[Fe(CN)_6]$ and $K_4[Fe(CN)_6]$, and incubated at 37° C. for 3-16 hours. After embedding in 7% agrose solution, sections (~100 μm) from fixed tissues were cut with a vibrotome (Campden Instruments, London, UK). Stained tissue was cleared of chlorophyll in 70% ethanol prior to visual examination under microscope.

Example 8

Statistical Analysis of GUS Activity Data

Because the gene expression in the populations of the first-generation transgenic plants usually does not follow a normal distribution, a non-parametric Mann-Whitney test was used for the distribution-free statistical analysis on the data.

Example 9

Structural Organization of the PR10 Gene (PmPR10-1.14) and Promoter

A 3140-bp DNA fragment of a PR10 gene (designated as PmPR10-1.14), including exonic, intronic, and flanking sequences, was isolated and determined (FIG. 1). To facilitate the sequence numbering, the first nucleotide of PmPR10 cDNA was designated as +1. The coding region of PmPR10-1.14 is 486 bp long and interrupted by an intron spanning 164 bp from +251 to +413. This intron position is highly conserved among PR10 protein genes from both angiosperm and gymnosperm plants. The 5'-exon/intron and 3'-intron/exon boundaries conformed to the known GT/AG donor/acceptor site rule. The intron is A/T-rich (66%), which is an essential characteristic for splicing. One poly (A) signal (AATAAT) is found at the position +767, 51 bp downstream of the stop codon (TAG). The coding region of cloned PR10 gene predicated a putative polypeptide of 161 amino acids with molecular mass of 17.96 kD and isoelectric point of 5.34. Alignment analysis of the deduced amino acid sequences showed that it shared 95% similarity with a PR10 cDNA (Pin m III) cloned previously from needles of western white pine, and belonged to a super gene family of PR10 proteins.

A putative transcription start site was identified which was an adenine just 2 base pairs ("bp") upstream of the first nucleotide of PR10 cDNA in western white pine. Inspection of upstream sequences revealed a TACAATAAATA motif SEQ.ID.NO. 16 at −34 as a potential TATA box and a putative CAAT 1 box located at −173.

To examine potential cis-regulatory elements, the promoter sequence of PmPR10-1.14 gene was analyzed (Quandt et al., 1995), to reveal a number of cis-regulatory elements that have been shown to be the binding sites of transcription factor proteins in angiosperms (Table I). Nineteen AAAG boxes were found throughout the whole promoter region, eleven of them in an inverse orientation. The AAAG elements are recognized by a class of plant-specific transcription factor-Dof proteins which may be involved in the expression of photosynthetic genes, genes of seed-storage proteins, a plant oncogene, and genes responsive to a plant hormone and/or stress signals. Nine gibberellin-responsive elements, i.e. TAACAAA-like boxes were detected at −1654,−1382,−1101,−997,−890,−793,−506,−497,−245, respectively; and five of them in an inverse orientation. TAACAAA-like box is conserved gibberellin (GA) response element in the promoters of GA-regulated genes of hydrolytic enzymes expressed in cereal aleurone cells. Two sequences homologous to the silencer consensus sequence, GGTTAA(A/T)(A/T)(A/T), were present at −1640 and −538, respectively. Another element, at position −273, GTGTGCTGACTT SEQ.ID.NO.17, matched in 10 of 12 positions the consensus sequence GGRTGCTGACGT SEQ.ID.NO.18, which is the binding site of transcription factor bZIP910 to regulate gene expression in a flower-preferential manner in Antirrhinum majus. Nucleotide sequences containing 10 to 12 nucleotides and being at least 80%, 90% or 95% homologous to SEQ.ID.NO.17 will in some instances be useful to enhance root-preferential or root-specific gene expression. This sequence will preferably be located between 0 and 500 nucleotides (more preferably between 50 and 350 or 100 and 200 nucleotides) on the 5' side of a promoter such as SEQ.ID.NO. 2. As one of most striking features of PmPR10-1.14 promoter, there are two highly conserved direct repeated sequences of 281 bp long located at 5'-distal region, sharing 97% similarity with each other. The repeated sequences are dispersed throughout the genomes of higher plants, some of which being identified in the promoter regions of plant genes. Some repeated sequences may be involved in various cellular functions, such as the regulation of gene, but the role of most repeative DNAs has not been elucidated.

Example 10

PmPR10-1.14 Promoter is Active Functionally in Agroinfiltrated Tobacco Leaves

Figure 3:
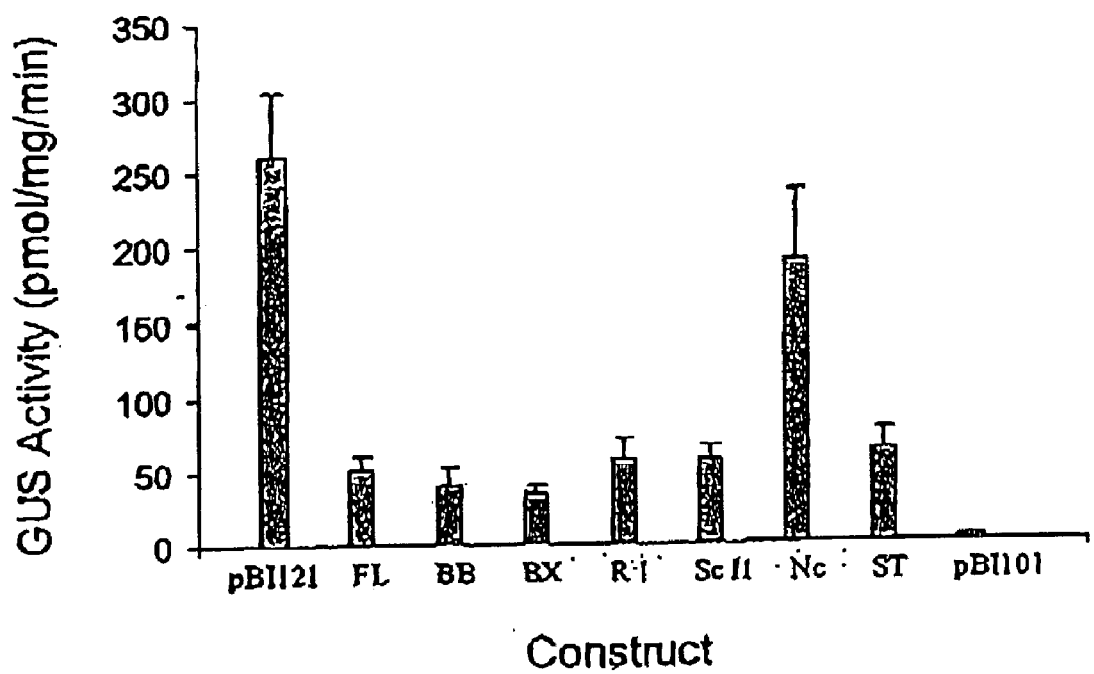
FIG. 3. is a graphical depiction of a fluorometric GUS assay in ago-infiltrated tobacco leaves carrying various PmPR10-1.14::GUS fusions. The GUS activities are expressed as pmol 4MU/mg protein/min. The bars represent the mean ±SD of the measurements from four independent experiments.

To investigate the functional properties of PmPR10-1.14 promoter, the relative activities of promoter regions deleted from 5'end of PR10-1.14 gene were tested directly by measuring the transient expression of promoter::GUS fusions in tobacco young leaves using agroinfiltration (Yang et al., 2000). Constructs of CaMV 35S promoter::GUS (pBI-121) and promoterless::GUS (pBI-101) were used as positive and negative controls, respectively. As shown in FIG. 2, a series of 5'-deletions of promoter fused to the uidA gene were constructed, and each of chimeric gene constructs was introduced into tobacco leaves by agroinfiltration. Four independent experiments were performed for the quantitative evaluation of GUS expression driven by PR10-1.14 promoter fragments. As shown in FIG. 8, all of the PmPR10-1.14 promoter::GUS fusions directed GUS gene expression actively, including construct ST that contained shortest promoter fragment from −101 to +69. In the negative control, GUS activity was not detectable in tobacco young leaves agroinfiltrated with the promoterless::GUS construct (pBI-101). Promoter sequence of PmPR10-1.14 gene from −101 to +69 the start site of coding region was sufficient to direct active transcription, indicating that this region contains sufficient cis-regulatory elements for the active gene expression in root tissue. No significant difference on the GUS activity levels was observed among all constructs of PmPR10-1.14 promoter::GUS fusions except the construct Nc with promoter sequence from −311 to +69. The construct Nc showed the highest level of GUS expression, which was 3 to 4 fold higher than other promoter constructs, almost at the same level as the CaMV 35S promoter (FIG. 3). This result demonstrated the presence of some negative cis-regulatory element(s) in the region from −506 to −311 and positive cis-regulatory element(s) in the region from −311 to −101. The activity of various promoter regions and fragments is shown in Table III.

Example 11

Root-Specific Expression of PmPR10-1.14::GUS Transgene in Transgenic Tobacco

To investigate the spatial and developmental regulation of PmPR10-1.14 gene, PmPR10-1.14 promoter::GUS fusions in the binary constructs (which were used to test promoter activity by analyzing transient gene expression) were transformed into tobacco plant for the analysis of stable gene expression. Transgenic tobacco plants with CaMV 35S promoter::GUS fusion of pBI-121, as a positive control, exhibited strong GUS activity in all organs and in seedlings. For the transformants of construct FL with longest promoter fragment from −1675 to +69 (SEQ ID No. 1), ten independent transgenic lines were selected randomly for fluorometric assay for GUS activity to monitor promoter activity in different organs. In the root organs of the transformants showed different intensities of GUS activity, the highest being six-fold more than the lowest (Table II). This variability of GUS expression is probably due to the position effect, the transcriptional activity of the region where the fusion gene was inserted. The GUS activity level differed enormously among the ten primary transformants. However, all showed a similar expression pattern of high level GUS activity in roots. Only low levels of GUS activity were measured in the extracts of other organs including leaves, stems, and flower organs (sepals, petals, stamen and pistils) (Table II). On average, the GUS activities in the roots were hundreds times higher than those in the leaves and stems. These differences were statistically significant.

Example 12

Figure 4:
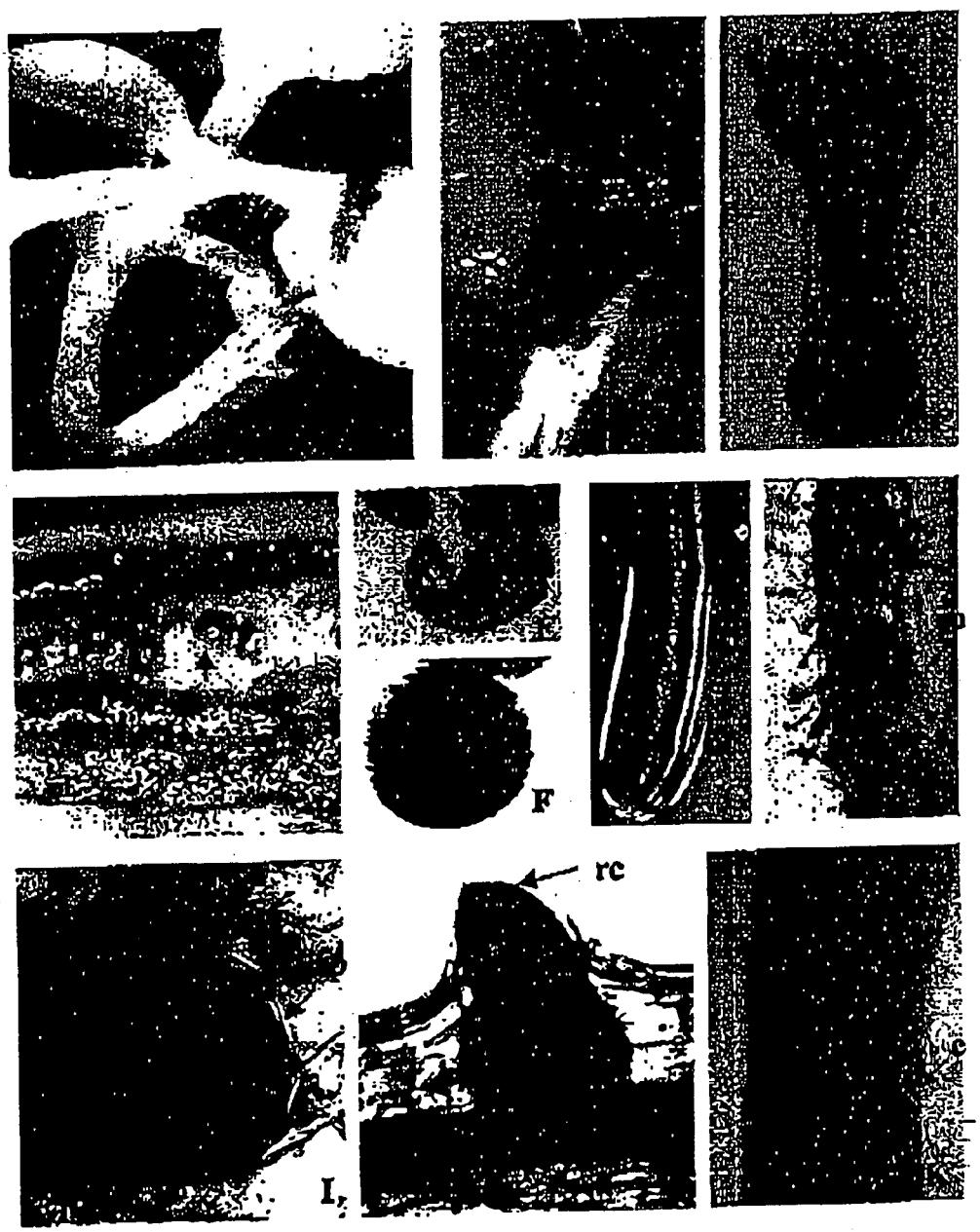
FIG. 4: is a depiction of the results of an In-situ histochemical localization of GUS activity in transgenic tobacco plants containing PmPR10-114::GUS fusion under control of the promoter sequence from +69 to −1675 in construct FL. A: 10-day old T2 seedling with GUS staining only in the root. B: the conjunction part of primary root and hypocotyl of the seedling in (A). C: the flower from T2 plants, half of it was removed to show stamen and pistil. D: longitudinal section of ovary showing a weak GUS staining in ovule in transgenic line F16. E: cross section of anther to show no signal in pollen grains. F: the developing embryo without signal. G: a lateral root showing root cap and root meristem part with strongest GUS activities. H: the zone of root hair from lateral roots. I: origin of the second lateral root primordium in the percycle of the primary root. J: the young lateral root tip growing out through the surrounding cortical tissue of the primary root with strongest GUS staining at root cap and meristem. K: longitudinal section of lateral root showing strong GUS staining in cortex tissue and no signal in vascular cylinder. am, apical meristem; c, cotyledons; cx, cortex; e, epidermis; hc, hypocotyl; lr, lateral roots; pr, primary roots; rc, root cap; rh, root hair; rp, root primordium; rv, root vascular cylinder; ow, ovary wall; pl, placenta; ov, ovule.

PmPR10-1.14. GUS Fusion is Specifically Regulated During the Development of Lateral Root Representative transgenic lines harboring construct FL of PmPR10-1.14 gene were allowed to self-pollinate and set seeds. At various times during seed germination, T2 plantlets were histochemically stained with X-Glue for GUS activity. GUS activity was observed for the first time in 6 to 8-day old seedlings when the lateral root began to develop, demonstrating that the root-specifically expression pattern of PmPR10-1.14 was controlled developmentally in transgenic tobacco seedlings (FIG. 4). At this developmental stage, in-situ GUS staining was only detected in the upper part of primary root connected to hypocotyl where the lateral-root was differentiating (FIG. 4A and B). Under microscope, the GUS activity was very strong in the primordium of lateral roots and also present low GUS staining level in the cortex cells of primary roots (FIG. 4-I and J). After the lateral root forced its way through the surrounding cortical tissue of the primary root, the strong GUS activity was observed in the tissues of root cap and meristem (FIG. 4-J and G). As the lateral root grew, the GUS activity was observed in the epidermis cell and root hair (FIG. 4-H). Analysis of longitudinal section of lateral roots revealed a high level of GUS expression in cortex cells, but no signal in the root vascular cylinder (FIG. 4-K). As plants grew up to mature stage, no GUS staining staining was observed in leaves, steins and flower organs, including petal, sepal, stamen and pitil (FIG. 4-C). Only transgenic line F16 was exception, and a little higher GUS expression was detected in the pistils (Table II). Observation of longitudinal section of ovarys of F16 T2 plants revealed a weak staining in the ovules (FIG. 4-D). The GUS activity was not detectable in the pollen grains from the mature anthers, embryos at different development stages (FIG. 4-F) and seeds even in transgenic line F16. These results demonstrated that PmPR10-1.14 gene in transgenic tobacco seedling was characteristically under the control of an exquisite tissue-specific expression program during the development of lateral roots. Thus, this promoter is useful in inducing root specific and/or root-preferential gene expression as well as inducing developmentally-regulated gene expression.

Example 13

The Spatial Expression of Endogeneous PR10 Gene in Western White Pine

Figure 5:
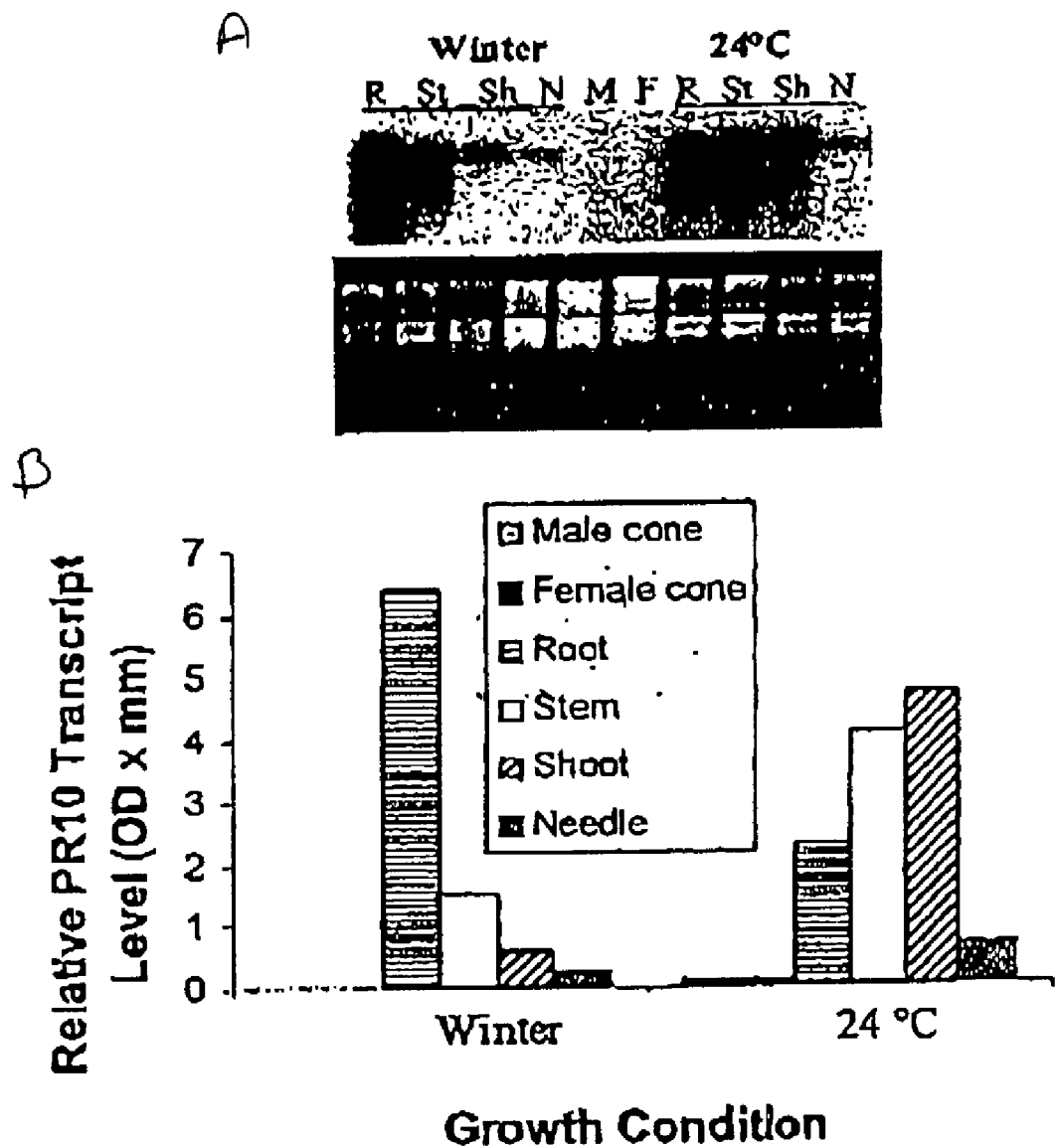
FIG. 5 is a pictorial (5a) and graphical (5b) depiction of the results of a northern blot analysis of PR10 gene expression in western white pine. The roots (R), stems (St), apical shoots (Sh), noodles (N) were collected from the seedlings growing natural condition in winter season (January 2000) and in growth chamber with conditions of 24° C. and lightness of 16-h day/8-h night. The immature male cones (M) and female cones (F) were collected from mature tree in May 2000. Top panel: X-ray film images of northern blots from different organs. 10 μg of total RNAs in each lane was hybridized with DNA probe from PmPR10-1.14. Middle panel; the ethidium bromide-stained gel as a loading control. Bottom panel: PR 10 transcript levels shown above were quantified using PDI software.
Figure 6:
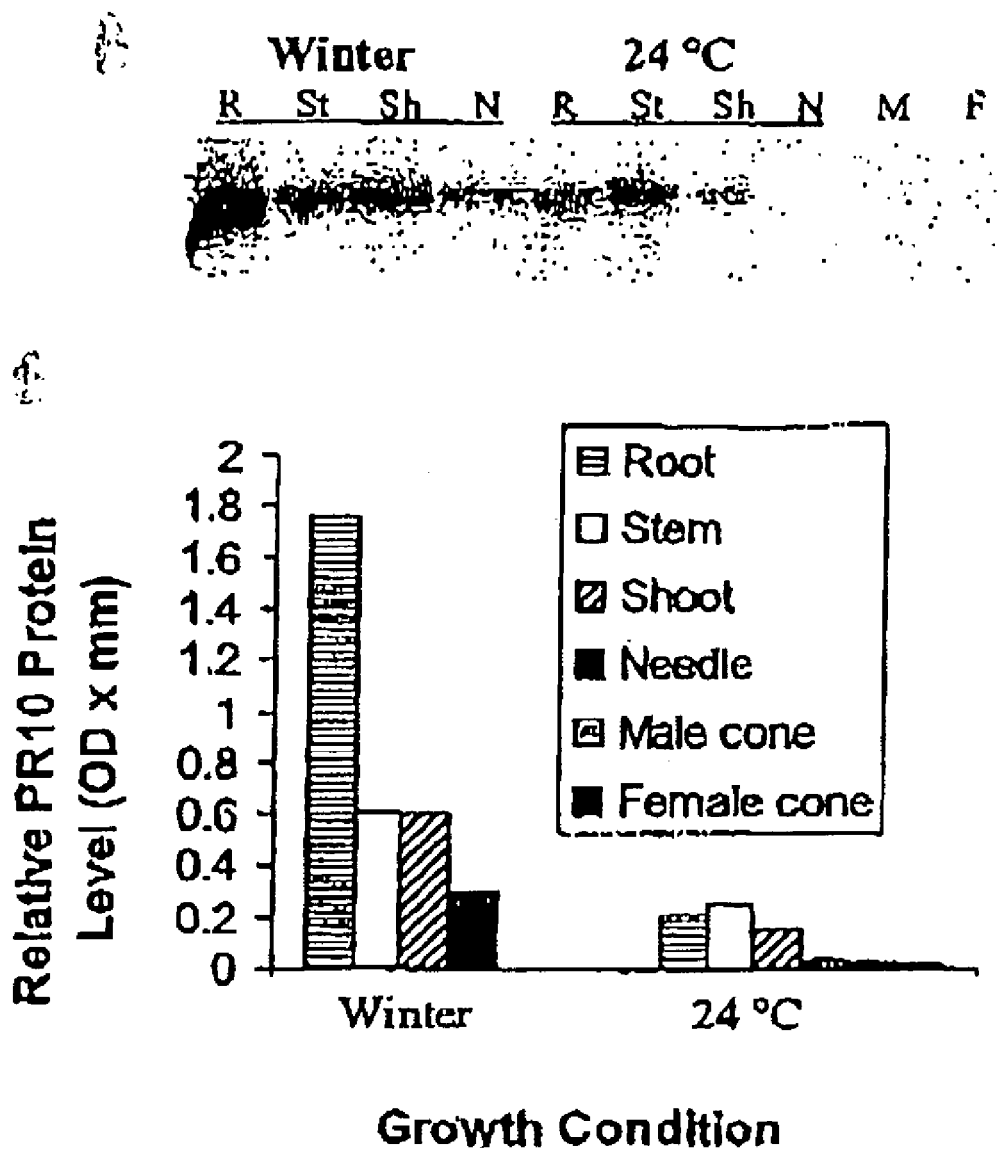
FIG. 6 is a pictorial (6a) and graphical (6b) depiction of the results of a western immunoblot analysis of PR10 protein level in different organs of western white pine. Tissue samples were the same as described in northern blot analysis. 10 μg of total protein was loaded in each lane, and separated by electrophoresis on SDS-polyacrylamide gels, blotted to PVDF membranes, and analyzed using an antiserium against the N-terminal region of a PR10 protein (Pin 1 I) from sugar pine. (Bottom) PR 10 protein levels shown above were quantified using PDI software.

To determine whether the behavior of the endogeneous white pine PR10 gene mimics that of the transgene, northern blot and Western immunoblot analysis were performed to monitor the expression profile established by the PR10 gene family, including PmPR10-1.14 gene. Because of high homology in the 3'-untranslated regions of PR10 gene members of western white pine, the accumulation of PR10 transcripts and proteins was analyzed in vegetative organs from seedlings, and developing reproductive organs from mature trees. Northern blot analyses showed that PR10 transcript was most abundant in the roots, followed by stems and vegetative shoots, and lowest level in needles in the winter of January 2000. (FIG. 5). But the tissue distribution of PR10 mRNAs was inverted under the conditions of temperature of 24° C. and photoperiod of 16-h day and 8-h night in growth chamber. PR10 mRNAs were accumulated at a highest level in apical shoots and stems, then in roots and low level in needles (FIG. 5). We further analyzed the tissue distribution of PR10 proteins under above two growth conditions. Western immunoblot analysis showed that the accumulation of PR10 proteins was at a high level in roots, followed by stems and apical shoots, and low level in needles in the winter month. By contrast, the PR10 proteins expressed at high level in stems and apical shoots, then in roots, lowest level in the needles of the seedlings from growth chamber (FIG. 6). Both PR10 transcript and protein were not detectable in the immature male cone and female cone collected from mature trees in May 2000 (FIGS. 5 and 6), similar to that observed for transgenes.

Figure 7:
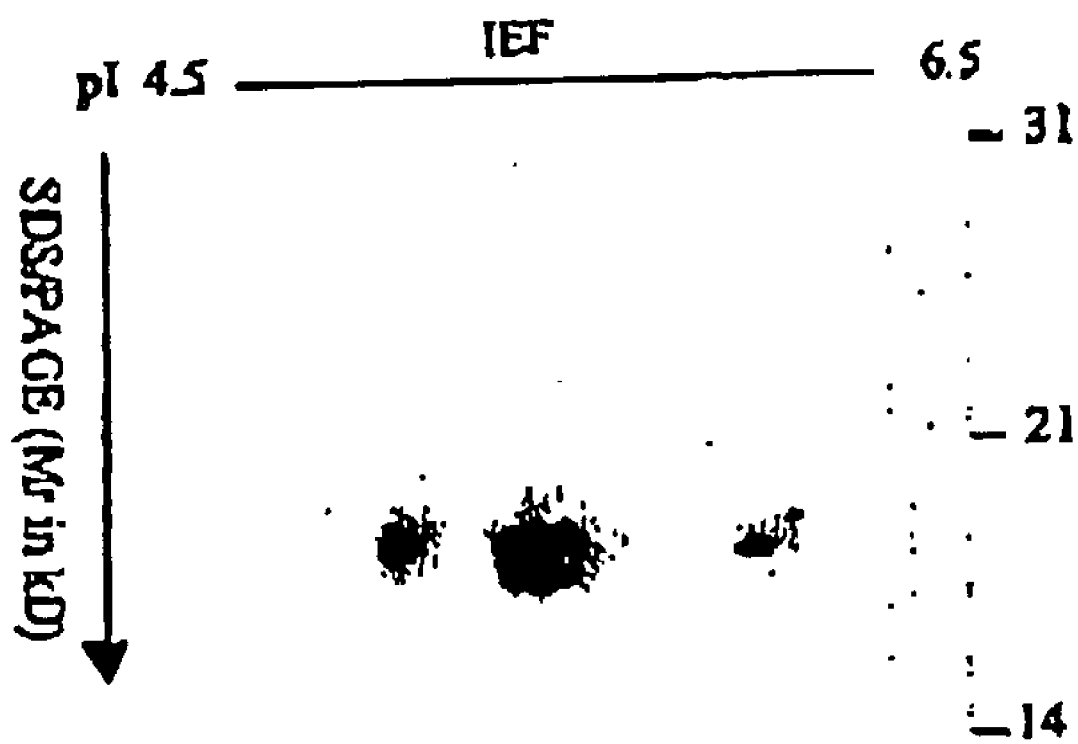
FIG. 7 is a depiction of a obtained PR10 protein profile from roots of western white pine using immunodetection of 2-D blots. For 2-D blots, the first dimension was IEF (pH 3-10), and second dimension was SDS-PAGE. 100 μg of total protein was loaded on IEF gel. The pI and position of each PR10 spot was determined by related migration rate with the references of standard proteins and recombinant PR10 protein of Pin m III from *E. coli*.

Because a multiple gene family of PR10 is present in western white pine, it is predicable multiple isoforms of PR10 protein are expressed. Western immunoblot analyses on 2-D blots showed that six PR10 isoforms were detected in the roots of seedlings from growth chamber (FIG. 7), These six isoforms could be divided into three groups according to their isoelectric points. Group I included two isoforms with pI about 5.9 to 6.0; group II contained three isoforms with pI about 5.5 to 5.6, but only one in group III with pI around 5.3. Group II was dominant, and PR10 isoform encoding by Pin m III fall into group II as predicated by the calculated pI value and confirmed by the analyses of its recombinant protein produced in *E. coli* (data not shown). According to the calculated pl and molecular mass, the isoform encoded by PmPR10-1.14 gene may belong to group III.

Example 14

The Effect or 281 bp Repeated Sequences on the Gene Expression in the Leaves and Stems of Transgenic Tobacco To reveal the promoter regions of PmPR10-1.14 gene that contain the cis-regulatory elements to mediate the root-specific expression, other constructs of PrPR10-1.14 promoter 5'-deletions (FIG. 2) were also transformed into tobacco to analyze stable gene expression. Different independent transgenic lines from each construct were selected to detect GUS activity in leaf and root of mature plants. As shown in FIG. 8, all of six constructs drove GUS gene expression at high levels in the roots and at low levels in leaves. As the promoter deleted from 5'-distal region to −311, the GUS activity showed a decreased trend in the roots, but the statistical analysis showed no significant difference for the gene activity in roots among six constructs. Furthermore, ratio of GUS activity in roots to those in leaves established by the −1675 bp promoter sequence (FL) was as high as 140 average, as the 5'-deletions continued to −311 bp, the ratio was still about 40 (FIG. 9), demonstrating that the cis-regulatory elements for the gene expression in roots may be present in the promoter region from −311 to +69.

As one of most striking features of PmPR10-1.14 promoter, it possesses two copies of repeated sequences as long as 281 bp from position −1600 to −1039. To study the functions of cis-regulation of these repeated sequences on gene expression, two constructs were made. In construct BB, one copy of the repeated sequence from −1326 to position −1045 was deleted; and in construct BX, both copies of the repeated sequences were deleted. Non-parametric statistical analysis of the transgenic T1 plants showed that the deletion of one copy or both copies of repeated sequences resulted in a significant increase of expression levels in leaves (p=0.014 between construct FL and BX; p=0.031 between construct BX and RI) (FIG. 8, below panel). The GUS activities in stems with construct BB and BX also showed a similar increase significantly (data not shown). But the gene expression was barely detectable in the flower tissues and developing seeds with these two constructs (data not shown). Further 5' deletion to −820 in construct R I recovered the gene expression pattern similar to that of construct FL again (FIG. 8). These results revealed that for the gene expression in the tissues of leaf and stem the repeated sequence of 281 bp functioned as a cis-regulatory element with negative effect and the sequence from −1045 to −820 as a cis-regulatory element with positive effect.

The following references may be of background interest with respect to methods described herein.

Ekramoddoullah A K M, Hunt R S (1993) Changes in protein profile of susceptible and resistant sugar pine foliage infected with the white pine blister rust fungus *Cronartium ribicola*. Can J Plant Pathol 15: 259-264.

Ekramoddoullab A K M, Davidson J J (1995) A method for the determination of conifer foliage protein extracted using sodium dodecyl sulfate and mercaptoethanol. Phytochem Anal 6: 20-24.

Ekramoddoullah A K M, Taylor D, Hawkins B J (1995) Characterization of a fall protein of sugar pine and detection of its homologue associated with frost hardiness of western white pine needles. Can J For Res 25: 1137-1147.

Horsch R B, Fry J E, Hoffman N L, Eichholtz D, Rogers S G, Fraley R T (1985) A simple and general method of transferring genes into plants. Science 227: 1229-1231.

Jefferson R A (1987) Assaying chimeric genes in plants: the GUS gene fulsion system. Plant Mol Biol Rep 5: 387-405.

Quandt K, Frech K, Karas H, Wingender E, Wemcr T (1995) MatInd and MatInspector—New fast and versatile tools for detection of consensus matches in nucleotide sequence data. Nucleic Acids Research 23: 4878-4884.

Sambrook J, Fritsch E F, Maniatis T (1989) Molecular Cloning: A Laboratory Manual, $2^{nd}$ ed., Cold Spring Harbor Laboratory, Cold Spring Harbor, N.Y.

Yang Y, Li R, Qi M (2000) In vivo analysis of plant promoters and transcription factors by agroinfiltration of tobacco leaves. Plant Journal 22(6): 543-551.

Yu X, Ekranoddoullah A K M, Misra S (2000) Characterization of Pin m III cDNA in western white pine. Tree Physiology 20: 663-671.

TABLE 1

The Putative Cis-Regulatory Elements in the PmPR101-1.14 Promoter

| Trans-Factor | Core Sequence[a] | Sequence[b] | Position |
|---|---|---|---|
| Dof/PBF | nnnwAAAGnnn | tttTAAAGgtt (+) | −55 to −45 |
| | | catTAAAGaga (−) | −72 to −62 |
| | | ctcGAAAGtga (−) | −110 to 100 |
| | | ccaCAAAGgcc (+) | −191 to −181 |

TABLE 1-continued

The Putative Cis-Regulatory Elements in the PmPR101-1.14 Promoter

| Trans-Factor | Core Sequence[a] | Sequence[b] | Position |
|---|---|---|---|
| | | tccTAAAGgac (−) | −238 to −228 |
| | | attCAAAGtca (+) | −278 to −268 |
| | | tgaCAAAGagt (−) | −398 to −388 |
| | | tgtCAAAGacg (−) | −566 to −556 |
| | | ctgAAAAGtca (+) | −653 to −643 |
| | | ttcAAAAGacc (−) | −689 to −679 |
| | | ataAAAAGatc (+) | −723 to −713 |
| | | agaAAAAGatt (−) | −743 to −733 |
| | | ccaTAAAGgtg (+) | −1019 to −1009 |
| | | ataGAAAGctg (+) | −1128 to −1118 |
| | | gctAAAAGttc (−) | −1223 to −1213 |
| | | attGAAAGctg (+) | −1349 to −1399 |
| | | gaaGAAAGtgg (+) | −1427 to −1417 |
| | | gatAAAAGtgc (−) | −1403 to −1393 |
| | | aggAAAAGagt (−) | −1770 to −1760 |
| GAMYB | YAACsrmm | CAACgatc (−) | −245 to −238 |
| | | CAACttcc (−) | −497 to −490 |
| | | TAACcacc (−) | −505 to −499 |
| | | CAACaaaa (+) | −793 to −886 |
| | | TAACggca (−) | −890 to −883 |
| | | CAACacc (+) | −996 to −989 |
| | | TAACtctc (+) | −1101 to −1094 |
| | | TAACtctc (+) | −1382 to −1375 |
| | | CAACaggt (−) | −1654 to −1647 |
| SBF1 | kwrTnGTTAAwwwn | gatggGTTAAgttc (+) | −538 to −525 |
| | | tagttGTTAAacat (+) | −1640 to −1627 |
| BZaP910 | GGRTGCTGACGT | GTGTGCTGACTT (−) | −273 to −262 |

[a] N = A + T + C + G, S = C + G, M = A + C Y = C + T, W = A + T, K = T + G, R = A + G, M = A + C
[b] (−), DNA sequence of antisense strand; (+), DNA sequence of sense strand

TABLE II

Fluorometric Quantification of GUS Activity in the Tissues of Different Transgenic Ti Plants Harboring PmPR10-1.14::GUS Fusion Vector FL. GUS activities in protein extracts were determined twice and expressed in pmol of 4-methylumbelliferyl-$\beta$-D-glucuronide/mg protein/min.

| Lines | Leaf | Stem | Root | Sepal | Petal | Stamen | Pistil | Root/Leaf | Root/Stem |
|---|---|---|---|---|---|---|---|---|---|
| FL2 | 31.35 | 33.88 | 3,413.33 | 16.29 | 30.06 | 29.86 | 9.95 | 108.15 | 100.74 |
| FL4 | 40.90 | 14.22 | 2,993.83 | 13.53 | 26.21 | 46.28 | 31.5 | 73.19 | 210.53 |
| FL6 | 26.57 | 24.67 | 2,621.21 | 16.54 | 14.81 | 10.13 | 9.52 | 98.65 | 106.25 |
| FL3 | 19.86 | 25.89 | 7,611.65 | 17.99 | 19.20 | 20.44 | 11.95 | 383.26 | 293.99 |
| FL9 | 23.22 | 51.46 | 3,666.67 | 18.12 | 10.95 | 17.31 | 9.46 | 157.91 | 71.25 |

TABLE II-continued

Fluorometric Quantification of GUS Activity in the Tissues of Different Transgenic Ti Plants Harboring PmPR10-1.14::GUS Fusion Vector FL. GUS activities in protein extracts were determined twice and expressed in pmol of 4-methylumbelliferyl-β-D-glucuronide/mg protein/min.

| Lines | Leaf | Stem | Root | Sepal | Petal | Stamen | Pistil | Root/Leaf | Root/Stem |
|---|---|---|---|---|---|---|---|---|---|
| FL8 | 11.29 | 20.66 | 1,294.63 | 28.57 | 16.60 | 4.19 | 4.44 | 114.67 | 62.66 |
| FL10 | 9.92 | 58.20 | 2,115.56 | 13.01 | 10.98 | 28.63 | 11.88 | 213.26 | 36.34 |
| FL5 | 26.57 | 17.22 | 2,482.53 | 17.46 | 9.79 | 42.62 | 20.00 | 93.43 | 144.16 |
| FL11 | 18.94 | 112.64 | 2,725.93 | 17.40 | 27.84 | 15.26 | 17.96 | 143.92 | 24.20 |
| FL16 | 51.93 | 113.56 | 1,983.84 | 31.57 | 39.51 | 88.19 | 242.04 | 38.20 | 17.42 |
| Mcan | 26.06 | 47.24 | 3,090.92 | 19.35 | 20.59 | 30.34 | 14.59 | 142.46 | 106.75 |
| ±SE | 9.40 | 29.38 | 1,191.05 | 5.87 | 8.24 | 12.05 | 6.42 | 65.69 | 65.68 |

TABLE IV

| Nt. Position | <1 | 1 | 2 | 3 | 4 | 5 | 6 | 7 | 8 | >1 | >2 |
|---|---|---|---|---|---|---|---|---|---|---|---|
| A | 0.16 | 0.03 | 0.95 | 0.00 | 1.00 | 0.62 | 0.97 | 0.38 | 0.73 | 0.13 | 0.30 |
| C | 0.63 | 0.01 | 0.00 | 0.04 | 0.00 | 0.00 | 0.00 | 0.01 | 0.08 | 0.42 | 0.42 |
| G | 0.05 | 0.00 | 0.00 | 0.00 | 0.00 | 0.00 | 0.02 | 0.00 | 0.10 | 0.28 | 0.16 |
| T | 0.16 | 0.96 | 0.05 | 0.96 | 0.00 | 0.38 | 0.01 | 0.61 | 0.09 | 0.18 | 0.11 |

We claim:

1. An isolated polynucleotide comprising the sequence as set forth in SEQ ID No. 2.

2. The isolated polynucleotide according to claim 1 comprising the sequence as set forth in SEQ ID No. 7.

3. The isolated polynucleotide according to claim 1 comprising the sequence as set forth in SEQ ID No. 5.

4. An isolated DNA sequence having activity as a root-specific promoter, said DNA sequence selected from the group consisting of SEQ ID NO. 1, SEQ ID NO. 5, SEQ ID NO. 6 and SEQ ID NO. 7.

5. An isolated DNA sequence having activity as a functional promoter in a plant cell, said DNA sequence comprising the sequence as set forth in SEQ ID No. 2.

6. A DNA construct comprising:
(a) a promoter sequence, in a sense orientation, said promoter sequence selected from the group consisting of SEQ ID No.1, SEQ ID No.2, SEQ ID No. 5, SEQ ID No. 6, SEQ No. 7;
(b) an open-reading frame polynucleotide coding for a polypeptide; and
(c) a termination sequence.

* * * * *

SEQUENCE LISTING

<160> NUMBER OF SEQ ID NOS: 25

<210> SEQ ID NO 1
<211> LENGTH: 1756
<212> TYPE: DNA
<213> ORGANISM: Pinus monticola

<400> SEQUENCE: 1

```
gaattctaat gaagatgact cttttcctgt gacacctgtt ggaccagtag ttgttaaaca      60
tcgagatcat acttccgcat ttagttccga agattctcgg ccaccttcaa cacaaaaatg     120
gcatagcatg agtgatatcc ttgatgatcc tgcctctatc cctctatttg aggaagatct     180
acaagcactt ttatctatgg agccatccat gcccatgcat gcctatatga tgcatggatc     240
tgatccacaa acttatgcag aagaaagtgg catcttgaat tgaaagctgc aatggatgag     300
gaatataact ctctcattga gaaatttgca agtgttggta aacttctaaa ccggtaacta     360
ggatccccga agattctcga ccaccttcaa cacaaaaatg gcgtagcatg agtgatatcc     420
ttgatgaccc tgcctctatc cctctatttg aggaagatct acaagaactt ttagctatgg     480
agccatccat gcccatgcat gcctatatga tgcatggatc tgatccacaa acttatgcag     540
aagcaagtgg gcatcttgaa tagaaagctg caatggatga ggaatataac tctctcattg     600
agaaatttgc aagtgttggt aaacttctaa accgtaact aggatcccta gggtggaaat      660
tatggattcc ataaaggtgc ggtgattact ccaacaccct ccccccatc aaacgcagct     720 cggagaatca atacacccct caaatgcact tggagggaat cgaacccggg tctatgctct     780
aataccatgt agaggtttgc cgttacacca aaacttgcaa gtgttgataa acttctaaac     840
agtagaatcc ccatgatgga aattatgaat tccatagaag tgtggtgatt actccaacaa     900
aatctaatcc atccataaaa atatacacaa actaattttc atttaatctt tttctgccca     960
tttaataaaa agatcaaaat tctggcagcc gaatatttgg tcttttgaac ttaacgaata    1020
tatatatata tccactgaaa agtcattttg aaatatatgc attccacggt agcgatggca    1080
```

```
cggcgttggt gaatgtagaa gccttcgtaa gcgatttacg gcgtctttga catttgtgta    1140
tctcttctag atgggttaac aacacggact gacaaaaccg cggtggttag ggaagttgga    1200
aacgatattc attgaaggat cagcctgtaa ataaataaat aaacacaaat tatccatttc    1260
atgtcttatc ttgttatctg gtcgtatcta ctctttgtca ttaatcgtct ctgtaagtgg    1320
gaaccggaac cggaatcgtc tcttgttgtt agatgagaag agaaataaca aatcaccatg    1380
ggatctagaa acatccatcc attccgttta ttcaaagtca gcacacacag tggggtccgg    1440
gggatcgttg tcctttagga cttatcgaaa ccaggcatgg agctcggtat tgtcggccac    1500
aaaggccaag ggttcaataa gaaaacccaa gtagttggca ttatgtgcgt ccatcggtca    1560
gtccaaataa caaatagtca ctttcgagtg gcttctcatg ccattaccta tgcgctctct    1620
ttaatgtaca gattttaaag gtttgtaaac gactacaata aatacgggct cgtctagtgc    1680
agttgagaac aaggagcttt gtgcgataat attgaagaaa tataagtatt gtgtagttgc    1740
gagagagttg aaaatg                                                    1756

<210> SEQ ID NO 2
<211> LENGTH: 170
<212> TYPE: DNA
<213> ORGANISM: Pinus monticola

<400> SEQUENCE: 2
agtggcttct catgccatta cctatgcgct ctctttaatg tacagatttt aaaggtttgt     60
aaacgactac aataaatacg ggctcgtcta gtgcagttga gaacaaggag ctttgtgcga    120
taatattgaa gaaatataag tattgtgtag ttgcgagaga gttgaaaatg                170

<210> SEQ ID NO 3
<211> LENGTH: 1195
<212> TYPE: DNA
<213> ORGANISM: Pinus monticola

<400> SEQUENCE: 3
gaattctaat gaagatgact cttttcctgt gacacctgtt ggaccagtag ttgttaaaca     60
tcgagatcat acttccgcat ttagttctag ggtggaaatt atggattcca taaaggtgcg    120
gtgattactc caacccctc cccccatca acgcagctc ggagaatcaa tacacccctc       180
aaatgcactt ggagggaatc gaacccgggt ctatgctcta ataccatgta gaggtttgcc    240
gttacaccaa aacttgcaag tgttgataaa cttctaaaca gtagaatccc catgatggaa    300
attatgaatt ccatagaagt gtggtgatta ctccaacaaa atctaatcca tccataaaaa    360
tatacacaaa ctaattttca tttaatcttt ttctgcccat ttaataaaaa gatcaaaatt    420
ctggcagccg aatatttggt cttttgaact taacgaatat atatatatat ccactgaaaa    480
gtcattttga aatatatgca ttccacggta gcgatggcac ggcgttggtg aatgtagaag    540
ccttcgtaag cgatttacgg cgtctttgac atttgtgtat ctcttctaga tgggttaaca    600
acacggactg acaaaaccgc ggtggttagg gaagttggaa acgatattca ttgaaggatc    660
agcctgtaaa taaataaata aacacaaatt atccatttca tgtcttatct tgttatctgg    720
tcgtatctac tctttgtcat taatcgtctc tgtaagtggg aaccggaacc ggaatcgtct    780
cttgttgtta gatgagaaga gaaataacaa atcaccatgg gatctagaaa catccatcca    840
ttccgtttat tcaaagtcag cacacacagt ggggtccggg ggatcgttgt cctttaggac    900
ttatcgaaac caggcatgga gctcggtatt gtcggccaca aaggccaagg gttcaataag    960
```

```
aaaacccaag tagttggcat tatgtgcgtc catcggtcag tccaaataac aaatagtcac   1020
tttcgagtgg cttctcatgc cattacctat gcgctctctt taatgtacag atttttaaagg  1080 tttgtaaacg actacaataa atacgggctc gtctagtgca gttgagaaca aggagctttg  1140
tgcgataata ttgaagaaat ataagtattg tgtagttgcg agagagttga aaatg        1195
```

<210> SEQ ID NO 4
<211> LENGTH: 1114
<212> TYPE: DNA
<213> ORGANISM: Pinus monticola

<400> SEQUENCE: 4

```
gatccctagg gtggaaatta tggattccat aaaggtgcgg tgattactcc aacaccctcc    60
cccccatcaa acgcagctcg gagaatcaat acacccctca aatgcacttg agggaatcg   120 aacccgggtc tatgctctaa taccatgtag aggtttgccg ttacaccaaa acttgcaagt  180
gttgataaac ttctaaacag tagaatcccc atgatggaaa ttatgaattc catagaagtg  240
tggtgattac tccaacaaaa tctaatccat ccataaaaat atacacaaac taattttcat   300
ttaatctttt tctgcccatt taataaaaag atcaaaattc tggcagccga atatttggtc   360
ttttgaactt aacgaatata tatatatatc cactgaaaag tcattttgaa atatatgcat   420
tccacggtag cgatggcacg gcgttggtga atgtagaagc cttcgtaagc gatttacggc   480
gtctttgaca tttgtgtatc tcttctagat gggttaacaa cacggactga caaaaccgcg   540
gtggttaggg aagttggaaa cgatattcat gaaggatca gcctgtaaat aaataaataa   600
acacaaatta tccatttcat gtcttatctt gttatctggt cgtatctact ctttgtcatt   660
aatcgtctct gtaagtggga accggaaccg gaatcgtctc ttgttgttag atgagaagag   720
aaataacaaa tcaccatggg atctagaaac atccatccat tccgtttatt caaagtcagc   780
acacacagtg gggtccgggg gatcgttgtc ctttaggact tatcgaaacc aggcatggag   840
ctcggtattg tcggccacaa aggccaaggg ttcaataaga aaacccaagt agttggcatt   900
atgtgcgtcc atcggtcagt ccaaataaca aatagtcact ttcgagtggc ttctcatgcc   960
attacctatg cgctctcttt aatgtacaga ttttaaaggt ttgtaaacga ctacaataaa  1020
tacgggctcg tctagtgcag ttgagaacaa ggagctttgt gcgataatat tgaagaaata  1080
taagtattgt gtagttgcga gagagttgaa aatg                             1114
```

<210> SEQ ID NO 5
<211> LENGTH: 889
<212> TYPE: DNA
<213> ORGANISM: Pinus monticola

<400> SEQUENCE: 5

```
aattccatag aagtgtggtg attactccaa caaaatctaa tccatccata aaaatataca    60
caaactaatt ttcatttaat ctttttctgc ccatttaata aaaagatcaa aattctggca   120
gccgaatatt tggtcttttg aacttaacga atatatatat atatccactg aaaagtcatt  180
ttgaaatata tgcattccac ggtagcgatg gcacggcgtt ggtgaatgta gaagccttcg   240
taagcgattt acggcgtctt tgacatttgt gtatctcttc tagatgggtt aacaacacgg   300
actgacaaaa ccgcggtggt tagggaagtt ggaaacgata ttcattgaag gatcagcctg   360
taaataaata aataaacaca attatccatt tcatgtcttt atcttgttat ctggtcgtat   420
ctactctttg tcattaatcg tctctgtaag tgggaaccgg aaccggaatc gtctcttgtt   480
gttagatgag aagagaaata acaaatcacc atgggatcta gaaacatcca tccattccgt   540
```

```
ttattcaaag tcagcacaca cagtggggtc cggggatcg ttgtccttta ggacttatcg     600
aaaccaggca tggagctcgg tattgtcggc cacaaaggcc aagggttcaa taagaaaacc    660
caagtagttg gcattatgtg cgtccatcgg tcagtccaaa taacaaatag tcactttcga    720
gtggcttctc atgccattac ctatgcgctc tctttaatgt acagatttta aggtttgta    780 aacgactaca ataaatacgg gctcgtctag tgcagttgag aacaaggagc tttgtgcgat    840
aatattgaag aaatataagt attgtgtagt tgcgagagag ttgaaaatg                889

<210> SEQ ID NO 6
<211> LENGTH: 575
<212> TYPE: DNA
<213> ORGANISM: Pinus monticola

<400> SEQUENCE: 6
ggtggttagg gaagttggaa acgatattca ttgaaggatc agcctgtaaa taaataaata     60
aacacaaatt atccatttca tgtcttatct tgttatctgg tcgtatctac tctttgtcat    120
taatcgtctc tgtaagtggg aaccggaacc ggaatcgtct cttgttgtta gatgagaaga    180
gaaataacaa atcaccatgg gatctagaaa catccatcca ttccgtttat tcaaagtcag    240
cacacacagt ggggtccggg ggatcgttgt cctttaggac ttatcgaaac caggcatgga    300
gctcggtatt gtcggccaca aggccaaggg ttcaataagg aaacccaag tagttggcat     360 tatgtgcgtc catcggtcag tccaaataac aaatagtcac tttcgagtgg cttctcatgc    420
cattacctat gcgctctctt taatgtacag attttaaagg tttgtaaacg actacaataa    480
atacgggctc gtctagtgca gttgagaaca aggagctttg tgcgataata ttgaagaaat    540
ataagtattg tgtagttgcg agagagttga aaatg                               575

<210> SEQ ID NO 7
<211> LENGTH: 380
<212> TYPE: DNA
<213> ORGANISM: Pinus monticola

<400> SEQUENCE: 7
catgggatct agaaacatcc atccattccg tttattcaaa gtcagcacac acagtggggt     60 ccggggatc gttgtccttt aggacttatc gaaccaggc atggagctcg gtattgtcgg     120
ccacaaaggc caagggttca ataagaaaac ccaagtagtt ggcattatgt gcgtccatcg    180
gtcagtccaa ataacaaata gtcactttcg agtggcttct catgccatta ctatgcgct    240 ctctttaatg tacagatttt aaaggtttgt aaacgactac aataaatacg gctcgtcta    300 gtgcagttga gaacaaggag ctttgtgcga taatattgaa gaaatataag tattgtgtag    360
ttgcgagaga gttgaaaatg                                                380

<210> SEQ ID NO 8
<211> LENGTH: 29
<212> TYPE: DNA
<213> ORGANISM: Artificial Sequence
<220> FEATURE:
<223> OTHER INFORMATION: Primer

<400> SEQUENCE: 8
ccttgcctcc acttgaacca cctcttccg                                      29

<210> SEQ ID NO 9
<211> LENGTH: 24
<212> TYPE: DNA
```

<213> ORGANISM: Artificial Sequence
<220> FEATURE:
<223> OTHER INFORMATION: Primer

<400> SEQUENCE: 9
cctctccaat cccaacttat actg                                    24

<210> SEQ ID NO 10
<211> LENGTH: 35
<212> TYPE: DNA
<213> ORGANISM: Artificial Sequence
<220> FEATURE:
<223> OTHER INFORMATION: Primer

<400> SEQUENCE: 10
aaaagcttct cgagatgact cttttcctgt gacac                        35

<210> SEQ ID NO 11
<211> LENGTH: 24
<212> TYPE: DNA
<213> ORGANISM: Artificial Sequence
<220> FEATURE:
<223> OTHER INFORMATION: Primer

<400> SEQUENCE: 11
catcggatag tatatggata gtgg                                    24

<210> SEQ ID NO 12
<211> LENGTH: 35
<212> TYPE: DNA
<213> ORGANISM: Artificial Sequence
<220> FEATURE:
<223> OTHER INFORMATION: Primer

<400> SEQUENCE: 12
aaggatccgt cgaccatttt caactctctc gcaac                        35

<210> SEQ ID NO 13
<211> LENGTH: 26
<212> TYPE: DNA
<213> ORGANISM: Artificial Sequence
<220> FEATURE:
<223> OTHER INFORMATION: Primer

<400> SEQUENCE: 13
aaaagcttag tggcttctca tgccat                                  26

<210> SEQ ID NO 14
<211> LENGTH: 24
<212> TYPE: DNA
<213> ORGANISM: Artificial Sequence
<220> FEATURE:
<223> OTHER INFORMATION: Polylinker oligonucleotide

<400> SEQUENCE: 14
acacaggaaa cagctatgac catg                                    24

<210> SEQ ID NO 15
<211> LENGTH: 24
<212> TYPE: DNA
<213> ORGANISM: Artificial Sequence
<220> FEATURE:
<223> OTHER INFORMATION: Primer

<400> SEQUENCE: 15
ggtttctaca ggacgtaaca taag                                    24

<210> SEQ ID NO 16
<211> LENGTH: 11
<212> TYPE: DNA
<213> ORGANISM: Pinus monticola

<400> SEQUENCE: 16
tacaataaat a                                                        11

<210> SEQ ID NO 17
<211> LENGTH: 12
<212> TYPE: DNA
<213> ORGANISM: Pinus monticola

<400> SEQUENCE: 17
gtgtgctgac tt                                                       12

<210> SEQ ID NO 18
<211> LENGTH: 12
<212> TYPE: DNA
<213> ORGANISM: Antirrhinum sp.

<400> SEQUENCE: 18
ggrtgctgac gt                                                       12

<210> SEQ ID NO 19
<211> LENGTH: 1475
<212> TYPE: DNA
<213> ORGANISM: Pinus monticola

<400> SEQUENCE: 19
gaattctaat gaagatgact cttttcctgt gacacctgtt ggaccagtag ttgttaaaca     60
tcgagatcat acttccgcat ttagttccga agattctcgg ccaccttcaa cacaaaaatg    120
gcatagcatg agtgatatcc ttgatgatcc tgcctctatc cctctatttg aggaagatct    180
acaagcactt ttatctatgg agccatccat gcccatgcat gcctatatga tgcatggatc    240
tgatccacaa acttatgcag aagaaagtgg catcttgaat tgaaagctgc aatggatgag    300
gaatataact ctctcattga gaaatttgca agtgttggta aacttctaaa ccggtaacta    360
ggatccctag ggtggaaatt atggattcca taaaggtgcg gtgattactc caacaccctc    420 cccccatca aacgcagctc ggagaatcaa tacacccctc aaatgcactt ggagggaatc    480
gaacccgggt ctatgctcta ataccatgta gaggtttgcc gttacaccaa acttgcaag    540 tgttgataaa cttctaaaca gtagaatccc catgatggaa attatgaatt ccatagaagt    600
gtggtgatta ctccaacaaa atctaatcca tccataaaaa tatacacaaa ctaattttca    660
tttaatcttt ttctgcccat ttaataaaaa gatcaaaatt ctggcagccg aatatttggt    720
cttttgaact taacgaatat atatatatat ccactgaaaa gtcatttga aatatatgca    780 ttccacggta gcgatggcac ggcgttggtg aatgtagaag ccttcgtaag cgatttacgg    840
cgtctttgac atttgtgtat ctcttctaga tgggttaaca acacggactg acaaaaccgc    900
ggtggttagg gaagttggaa acgatattca ttgaaggatc agcctgtaaa taataaata    960 aacacaaatt atccatttca tgtcttatct tgttatctgg tcgtatctac tctttgtcat   1020
taatcgtctc tgtaagtggg aaccggaacc ggaatcgtct cttgttgtta gatgagaaga   1080
gaaataacaa atcaccatgg gatctagaaa catccatcca ttccgtttat tcaaagtcag   1140
cacacacagt ggggtccggg ggatcgttgt cctttaggac ttatcgaaac caggcatgga   1200

-continued

```
gctcggtatt gtcggccaca aaggccaagg gttcaataag aaaacccaag tagttggcat    1260
tatgtgcgtc catcggtcag tccaaataac aaatagtcac tttcgagtgg cttctcatgc    1320
cattacctat gcgctctctt taatgtacag attttaaagg tttgtaaacg actacaataa    1380
atacgggctc gtctagtgca gttgagaaca aggagctttg tgcgataata ttgaagaaat    1440
ataagtattg tgtagttgcg agagagttga aaatg                               1475
```

<210> SEQ ID NO 20
<211> LENGTH: 3140
<212> TYPE: DNA
<213> ORGANISM: Pinus monticola
<220> FEATURE:
<221> NAME/KEY: CDS
<222> LOCATION: (1754)..(1936)
<220> FEATURE:
<221> NAME/KEY: CDS
<222> LOCATION: (2101)..(2400)

<400> SEQUENCE: 20

```
gaattctaat gaagatgact cttttcctgt gacacctgtt ggaccagtag ttgttaaaca     60
tcgagatcat acttccgcat ttagttccga agattctcgg ccaccttcaa cacaaaaatg    120
gcatagcatg agtgatatcc ttgatgatcc tgcctctatc cctctatttg aggaagatct    180
acaagcactt ttatctatgg agccatccat gcccatgcat gcctatatga tgcatggatc    240
tgatccacaa acttatgcag aagaaagtgg catcttgaat tgaaagctgc aatggatgag    300
gaatataact ctctcattga gaaatttgca agtgttggta aacttctaaa ccggtaacta    360
ggatccccga agattctcga ccaccttcaa cacaaaaatg gcgtagcatg agtgatatcc    420
ttgatgaccc tgcctctatc cctctatttg aggaagatct acaagaactt ttagctatgg    480
agccatccat gcccatgcat gcctatatga tgcatggatc tgatccacaa acttatgcag    540
aagcaagtgg gcatcttgaa tagaaagctg caatggatga ggaatataac tctctcattg    600
agaaatttgc aagtgttggt aaacttctaa accggtaact aggatcccta gggtggaaat    660
tatggattcc ataaaggtgc ggtgattact ccaacaccct cccccccatc aaacgcagct    720
cggagaatca atacacccct caaatgcact tggagggaat cgaacccggg tctatgctct    780
aataccatgt agaggtttgc cgttacacca aaacttgcaa gtgttgataa acttctaaac    840
agtagaatcc ccatgatgga aattatgaat tccatagaag tgtggtgatt actccaacaa    900
aatctaatcc atccataaaa atatacacaa actaattttc atttaatctt tttctgccca    960
tttaataaaa agatcaaaat tctggcagcc gaatatttgg tcttttgaac ttaacgaata   1020
tatatatata tccactgaaa agtcattttg aaatatatgc attccacggt agcgatggca   1080
cggcgttggt gaatgtagaa gccttcgtaa gcgatttacg gcgtctttga catttgtgta   1140
tctcttctag atgggttaac aacacggact gacaaaaccg cggtggttag ggaagttgga   1200
aacgatattc attgaaggat cagcctgtaa ataaataaat aaacacaaat tatccatttc   1260
atgtcttatc ttgttatctg gtcgtatcta ctctttgtca ttaatcgtct ctgtaagtgg   1320
gaaccggaac cggaatcgtc tcttgttgtt agatgagaag agaataaca aatcaccatg    1380 ggatctagaa acatccatcc attccgttta ttcaaagtca gcacacacag tggggtccgg   1440
gggatcgttg tcctttagga cttatcgaaa ccaggcatgg agctcggtat tgtcggccac   1500
aaaggccaag ggttcaataa gaaaacccaa gtagttggca ttatgtgcgt ccatcggtca   1560
gtccaaataa caaatagtca ctttcgagtg gcttctcatg ccattaccta tgcgctctct   1620
ttaatgtaca gattttaaag gtttgtaaac gactacaata aatacgggct cgtctagtgc   1680
```

```
agttgagaac aaggagcttt gtgcgataat attgaagaaa tataagtatt gtgtagttgc    1740
gagagagttg aaa atg gtg tca ggg act tca tca acg gaa gag gtg gtt       1789
            Met Val Ser Gly Thr Ser Ser Thr Glu Glu Val Val
            1               5                   10
caa gtg gag gca agg agg ttg tgg aac gcc aca acg aaa gac ggc cac      1837
Gln Val Glu Ala Arg Arg Leu Trp Asn Ala Thr Thr Lys Asp Gly His
 15                  20                  25
gac ttc ttg cca aag gtt ttg ccc gaa gtt ttt act tct gtc acc tta      1885
Asp Phe Leu Pro Lys Val Leu Pro Glu Val Phe Thr Ser Val Thr Leu
 30                  35                  40
ctt caa gga gat gga ggc gtc ggc acc gtc aag cag ctc aat ttc acc      1933
Leu Gln Gly Asp Gly Gly Val Gly Thr Val Lys Gln Leu Asn Phe Thr
45                  50                  55                  60
cct ggtataactc ccatacatac ttttgttgat cacatatcat tgttaacatc           1986
Pro
actataattc cacttctaat tattcccccg catgaattag cgtagcagat gcagatgggg    2046
ttgaagatta ttttattatt taacacttgc atggttttc actttacttt gaca ggt       2103
                                                            Gly
aag aag gat ttc agc ttc atc aag gag cga gtg gat gaa ctt gac gag      2151
Lys Lys Asp Phe Ser Phe Ile Lys Glu Arg Val Asp Glu Leu Asp Glu
             65                  70                  75
gag aat ttt gtg tat aag tat aca gcg atc gaa gga gga ccg ctg ggg      2199
Glu Asn Phe Val Tyr Lys Tyr Thr Ala Ile Glu Gly Gly Pro Leu Gly
 80                  85                  90
aag aaa ctg agc tct gcg tgc ctt gag gtg aaa ttg gtt cct agg aaa      2247
Lys Lys Leu Ser Ser Ala Cys Leu Glu Val Lys Leu Val Pro Arg Lys
95                  100                 105                 110
gaa ggg gga tgc gta gcg agg tgg acc tgt aac tac gaa act ctt cct      2295
Glu Gly Gly Cys Val Ala Arg Trp Thr Cys Asn Tyr Glu Thr Leu Pro
                115                 120                 125
ggt gtt caa cct gac gaa gga aaa ttt aaa gag ata aag gaa gat agc      2343
Gly Val Gln Pro Asp Glu Gly Lys Phe Lys Glu Ile Lys Glu Asp Ser
                130                 135                 140
ttt ggc atg ttg aag aaa gtg gag cag tat ctc ctc tcc aat ccc aac      2391
Phe Gly Met Leu Lys Lys Val Glu Gln Tyr Leu Leu Ser Asn Pro Asn
145                 150                 155
tta tac tgc tagatatgtt tacgtatgca taaatagtgt agagccgcac              2440
Leu Tyr Cys
    160
gttcaacgtg caaaataatg gagagtcacg atatgacttc ctcccaccgt cattgtcgtt    2500
tatgggccgt cggatgcctt tgttatgcct ttatcgttac gtgattgtgt gtagttctgt    2560
gaattcaaat caatgtcaac gttcgttcag tattgtgtgt tcagagcaaa ttcgactcct    2620
ttttattcac ttttcaaatc accccgacag caatcccatt ttatacgata aatgggtatt    2680
tttcgttaca aattagatta ttaattttttt ttaggttcat atccactttc cactatccat   2740
atactatggc atgaattaaa actatggaag aattgatttg caatttcatt tagagggggat   2800 atctatttta atttttgcatt tatctatttta atgttagagc aggtgctaca acgtagctac  2860
tagtagttta gtttaattta aatatagtaa tgctgcaatc ttattttgaa aatgtttatg    2920
ttactttgca ataaagttga tttcaaagtt tctctatttt tgcactatat taaaattatt    2980
ctaaaaatgt ttttaaaaaa acttgatcat aaccattaat aaaccagtta tttttgttct    3040
taattgctct cggaaaactt tactgtcata tgtgcatttg tatgctttct tgttttaaca    3100
aaattttgca aacacgttgt acgttgagag aggaggatcc                          3140

<210> SEQ ID NO 21
```

```
<211> LENGTH: 211
<212> TYPE: DNA
<213> ORGANISM: Pinus monticola

<400> SEQUENCE: 21
catgggatct agaaacatcc atccattccg tttattcaaa gtcagcacac acagtggggt    60
ccgggggatc gttgtccttt aggacttatc gaaaccaggc atggagctcg gtattgtcgg   120
ccacaaaggc caagggttca ataagaaaac ccaagtagtt ggcattatgt gcgtccatcg   180
gtcagtccaa ataacaaata gtcactttcg a                                  211

<210> SEQ ID NO 22
<211> LENGTH: 195
<212> TYPE: DNA
<213> ORGANISM: Pinus monticola

<400> SEQUENCE: 22
ggtggttagg gaagttggaa acgatattca ttgaaggatc agcctgtaaa taataaata     60 aacacaaatt atccatttca tgtcttatct tgttatctgg tcgtatctac tctttgtcat   120
taatcgtctc tgtaagtggg aaccggaacc ggaatcgtct cttgttgtta gatgagaaga   180
gaaataacaa atcac                                                    195

<210> SEQ ID NO 23
<211> LENGTH: 11
<212> TYPE: DNA
<213> ORGANISM: Pinus monticola
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (9)..(11)
<223> OTHER INFORMATION: n is a, c, g, or t

<400> SEQUENCE: 23
nnnwaaagnn n                                                         11

<210> SEQ ID NO 24
<211> LENGTH: 161
<212> TYPE: PRT
<213> ORGANISM: Pinus monticola

<400> SEQUENCE: 24

Met Val Ser Gly Thr Ser Ser Thr Glu Glu Val Gln Val Glu Ala
1               5                   10                  15

Arg Arg Leu Trp Asn Ala Thr Thr Lys Asp Gly His Asp Phe Leu Pro
            20                  25                  30

Lys Val Leu Pro Glu Val Phe Thr Ser Val Thr Leu Leu Gln Gly Asp
        35                  40                  45

Gly Gly Val Gly Thr Val Lys Gln Leu Asn Phe Thr Pro Gly Lys Lys
    50                  55                  60

Asp Phe Ser Phe Ile Lys Glu Arg Val Asp Glu Leu Asp Glu Glu Asn
65                  70                  75                  80

Phe Val Tyr Lys Tyr Thr Ala Ile Glu Gly Gly Pro Leu Gly Lys Lys
                85                  90                  95

Leu Ser Ser Ala Cys Leu Glu Val Lys Leu Val Pro Arg Lys Glu Gly
            100                 105                 110

Gly Cys Val Ala Arg Trp Thr Cys Asn Tyr Glu Thr Leu Pro Gly Val
        115                 120                 125
```

```
Gln Pro Asp Glu Gly Lys Phe Lys Glu Ile Lys Glu Asp Ser Phe Gly
    130                 135                 140

Met Leu Lys Lys Val Glu Gln Tyr Leu Leu Ser Asn Pro Asn Leu Tyr
145                 150                 155                 160

Cys

<210> SEQ ID NO 25
<211> LENGTH: 14
<212> TYPE: DNA
<213> ORGANISM: Pinus monticola
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t

<400> SEQUENCE: 25
kwrtngttaa wwwn                                                      14
```